(12) United States Patent
Han et al.

(10) Patent No.: US 9,193,768 B2
(45) Date of Patent: Nov. 24, 2015

(54) PEPTIDE FOR INHIBITION OF BINDING BETWEEN ANGIOPOIETIN-2 AND INTEGRIN AND USE THEREOF

(71) Applicant: Samsung Electronics Co., Ltd., Suwon-si, Gyeonggi-do (KR)

(72) Inventors: Sang Yeul Han, Yongin-si (KR); Chung Ho Kim, Yongin-si (KR); Kyung Eun Kim, Yongin-si (KR); Hyung-Chan Kim, Yongin-si (KR); Kwang-Hoon Lee, Osan-si (KR); Hyo Seon Lee, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/058,069

(22) Filed: Oct. 18, 2013

(65) Prior Publication Data

US 2014/0113858 A1    Apr. 24, 2014

(30) Foreign Application Priority Data

Oct. 18, 2012   (KR) .......................... 10-2012-0116155

(51) Int. Cl.
*C07K 14/00* (2006.01)
*C07K 14/515* (2006.01)
*A61K 38/00* (2006.01)

(52) U.S. Cl.
CPC ............... *C07K 14/001* (2013.01); *C07K 14/00* (2013.01); *C07K 14/515* (2013.01); *A61K 38/00* (2013.01)

(58) Field of Classification Search
CPC ..... C07K 14/001; C07K 14/515; A61K 38/00
See application file for complete search history.

(56) References Cited

U.S. PATENT DOCUMENTS

| | | | |
|---|---|---|---|
| 6,265,564 B1 * | 7/2001 | Davis et al. ................. | 536/23.5 |
| 2003/0194373 A1 | 10/2003 | Fauconnier et al. | |
| 2005/0186662 A1 * | 8/2005 | Low ............................ | 435/69.4 |
| 2011/0158978 A1 | 6/2011 | Kirchner et al. | |
| 2012/0052073 A1 | 3/2012 | Green et al. | |
| 2012/0100166 A1 | 4/2012 | Roschke et al. | |
| 2012/0141499 A1 | 6/2012 | Oliner et al. | |
| 2012/0142091 A1 | 6/2012 | Brinkmann et al. | |

OTHER PUBLICATIONS

Augustin et al., "Control of Vascular morphogenesis and homeostasis through the angiopoietin-Tie system", *Mol. Cell Biol.*, (10) 165-177 (2009).
Felcht et al., "Angiopoietin-2 differentially regulates angiogenesis through TIE2 and integrin signaling", *Jour. of Clin. Inv.*, pp. 1-15 (2012).
Hanahan et al., "Signaling Vascular Morphogenesis and Maintenance", *Science*, 277 (5322), pp. 48-50 (1997).
Holopainen et al., "Effects of Angiopoietin-2-Blocking Antibody on Endothelial Cell-Cell Junctions and Lung Metastasis", *J. Natl Cancer Inst.*, (104):461-475 (2012).
Hu et al., "Angiopoietin 2 Induces Glioma Cell Invasion by Stimulating Matrix Metalloprotease 2 Expression through the αvβ1 Integrin and Focal Adhesion Kinase Signaling Pathway", *Cancer Research*, 66 (2):775-783 (Jan. 15, 2006).
Imanishi et al, "Angiopoietin 2 Stimulates Breast Cancer Metastasis through the αvβ1 Integrin-Mediated Pathway", *Cancer Research*, pp. 4254-4263 (May 1, 2007).
Maisonpierre et al., "Angiopoietin 2, a Natural Antagonist for Tie2 That Disrupts in vivo Angiogenesis", *Science*, (277) 55-60, (Jul. 4, 1997).

* cited by examiner

*Primary Examiner* — Ruixiang Li
(74) *Attorney, Agent, or Firm* — Leydig, Voit & Mayer, Ltd.

(57) ABSTRACT

There are provided an angiopoietin-2 (Ang2) derived peptides, polypeptides, and peptide complexes, and a method for inhibition of binding between Ang2 and integrin and prevention and/or treatment of a disease caused by the activation of Ang2 or the binding between Ang2 and integrin using the peptide, polypeptides, and peptide complexes.

9 Claims, 18 Drawing Sheets
(5 of 18 Drawing Sheet(s) Filed in Color)

FIG. 4
Poly-L-Lysine
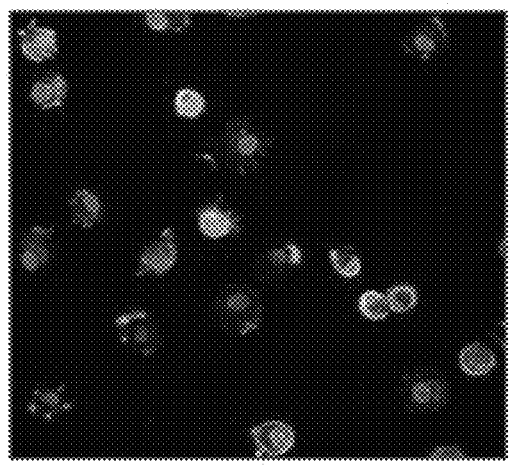
Fibronectin
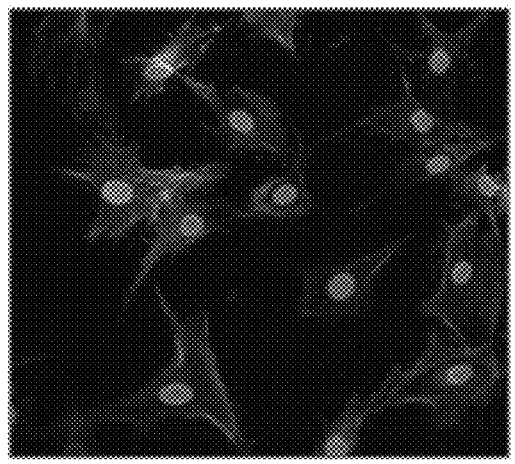
Ang2
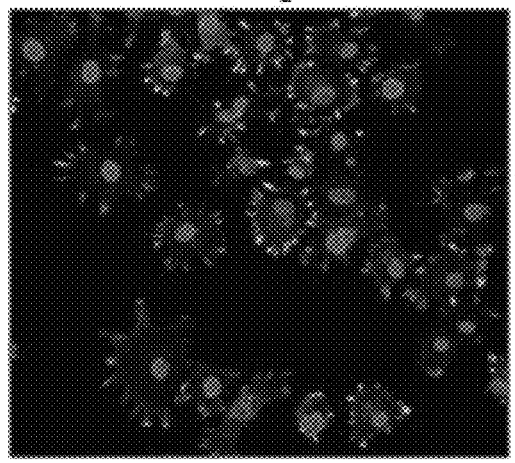
F-Actin/Nucleus FIG. 14
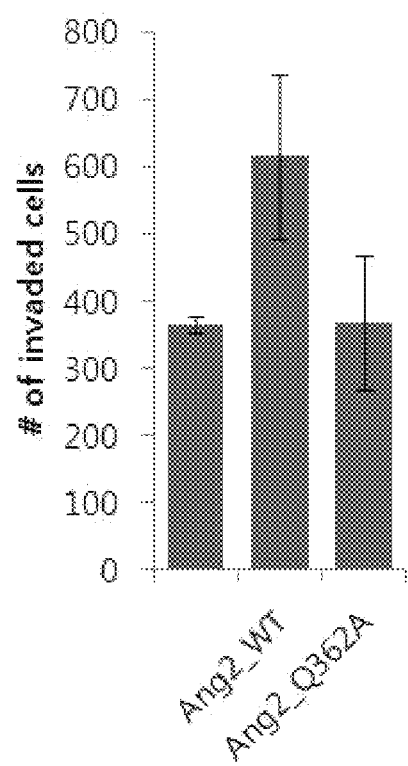

FIG. 17
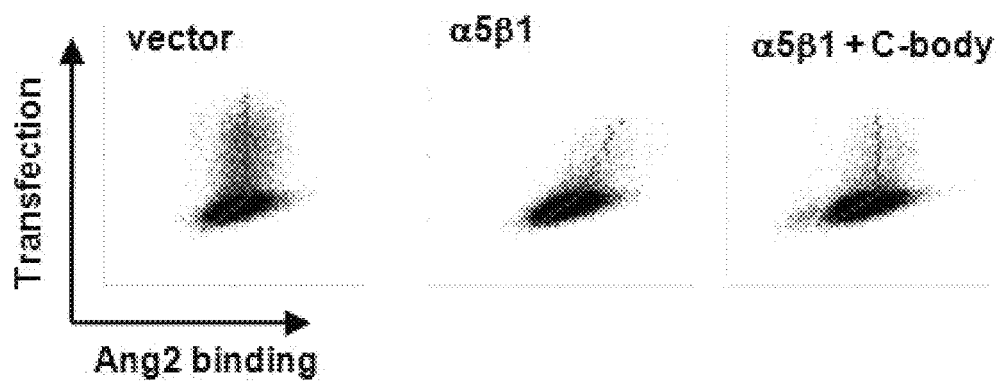
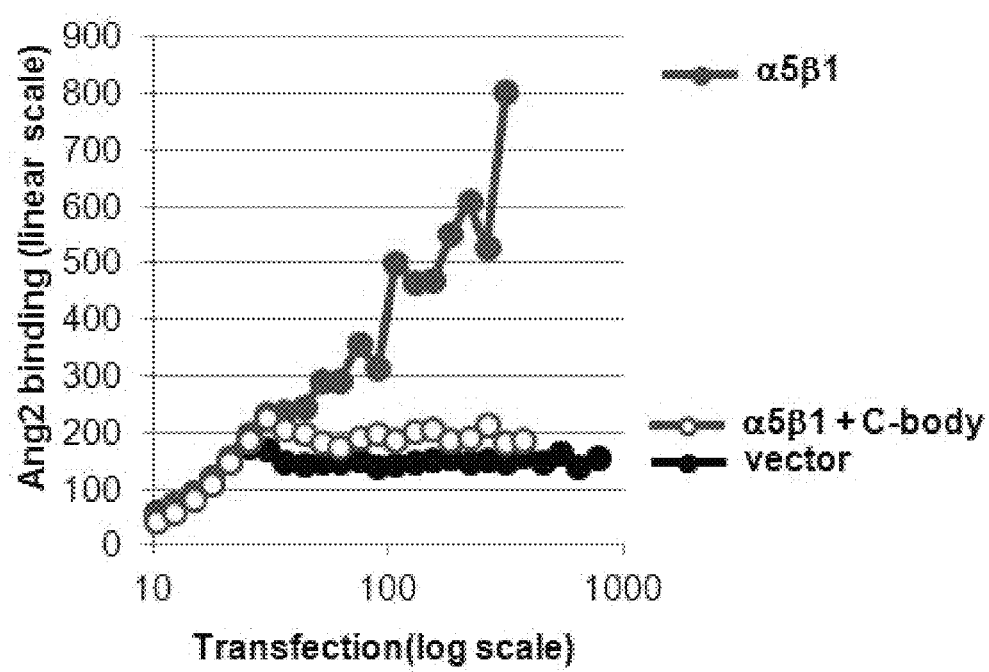

SEQUENCE LISTING

```
<160> NUMBER OF SEQ ID NOS: 44

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide 1

<400> SEQUENCE: 1

Arg Asp Cys Ala Glu Val Phe Lys Ser Gly His Thr Thr Asn Gly
1               5                   10                  15

<210> SEQ ID NO 2
```

-continued

```
<211> LENGTH: 15
<212> TYPE: PRT
<213> ORGANISM: Artificial Sequence
<220> FEATURE:
<223> OTHER INFORMATION: Synthetic Peptide 2

<400> SEQUENCE: 2

Val Phe Lys Ser Gly His Thr Thr Asn Gly Ile Tyr Thr Leu Thr
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide 3

<400> SEQUENCE: 3

His Thr Thr Asn Gly Ile Tyr Thr Leu Thr Phe Pro Asn Ser Thr
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide 4

<400> SEQUENCE: 4

Ile Tyr Thr Leu Thr Phe Pro Asn Ser Thr Glu Glu Ile Lys Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic Peptide 5

<400> SEQUENCE: 5

Phe Pro Asn Ser Thr Glu Glu Ile Lys Ala Tyr Cys Asp Met Glu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic Peptide 6

<400> SEQUENCE: 6

Glu Glu Ile Lys Ala Tyr Cys Asp Met Glu Ala Gly Gly Gly Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide 7

<400> SEQUENCE: 7

Tyr Cys Asp Met Glu Ala Gly Gly Gly Gly Trp Thr Ile Ile Gln
1               5                   10                  15

<210> SEQ ID NO 8
<211> LENGTH: 15
```

```
<212> TYPE: PRT
<213> ORGANISM: Artificial Sequence
<220> FEATURE:
<223> OTHER INFORMATION: Synthetic Peptide 8

<400> SEQUENCE: 8

Ala Gly Gly Gly Gly Trp Thr Ile Ile Gln Arg Arg Glu Asp Gly
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Peptide 9

<400> SEQUENCE: 9

Trp Thr Ile Ile Gln Arg Arg Glu Asp Gly Ser Val Asp Phe Gln
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Peptide 10

<400> SEQUENCE: 10

Arg Arg Glu Asp Gly Ser Val Asp Phe Gln Arg Thr Trp Lys Glu
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide 11

<400> SEQUENCE: 11

Ser Val Asp Phe Gln Arg Thr Trp Lys Glu Tyr Lys Val Gly Phe
 1               5                  10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide 12

<400> SEQUENCE: 12

Arg Thr Trp Lys Glu Tyr Lys Val Gly Phe Gly Asn Pro Ser Gly
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide 13

<400> SEQUENCE: 13

Tyr Lys Val Gly Phe Gly Asn Pro Ser Gly Glu Tyr Trp Leu Gly
 1               5                  10                  15

<210> SEQ ID NO 14
<211> LENGTH: 15
<212> TYPE: PRT
```

-continued

```
<213> ORGANISM: Artificial Sequence
<220> FEATURE:
<223> OTHER INFORMATION: Synthetic Peptide 14

<400> SEQUENCE: 14

Gly Asn Pro Ser Gly Glu Tyr Trp Leu Gly Asn Glu Phe Val Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide 15

<400> SEQUENCE: 15

Glu Tyr Trp Leu Gly Asn Glu Phe Val Ser Gln Leu Thr Asn Gln
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide 16

<400> SEQUENCE: 16

Asn Glu Phe Val Ser Gln Leu Thr Asn Gln Gln Arg Tyr Val Leu
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide 17

<400> SEQUENCE: 17

Gln Leu Thr Asn Gln Gln Arg Tyr Val Leu Lys Ile His Leu Lys
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide 18

<400> SEQUENCE: 18

Gln Arg Tyr Val Leu Lys Ile His Leu Lys Asp Trp Glu Gly Asn
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide 19

<400> SEQUENCE: 19

Lys Ile His Leu Lys Asp Trp Glu Gly Asn Glu Ala Tyr Ser Leu
1               5                   10                  15

<210> SEQ ID NO 20
<211> LENGTH: 15
<212> TYPE: PRT
<213> ORGANISM: Artificial Sequence
```

-continued

```
<220> FEATURE:
<223> OTHER INFORMATION: Synthetic Peptide 20

<400> SEQUENCE: 20

Asp Trp Glu Gly Asn Glu Ala Tyr Ser Leu Tyr Glu His Phe Tyr
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide 21

<400> SEQUENCE: 21

Glu Ala Tyr Ser Leu Tyr Glu His Phe Tyr Leu Ser Ser Glu Glu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic Peptide 22

<400> SEQUENCE: 22

Tyr Glu His Phe Tyr Leu Ser Ser Glu Glu Leu Asn Tyr Arg Ile
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide 23

<400> SEQUENCE: 23

Leu Ser Ser Glu Glu Leu Asn Tyr Arg Ile His Leu Lys Gly Leu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic Peptide 24

<400> SEQUENCE: 24

Leu Asn Tyr Arg Ile His Leu Lys Gly Leu Thr Gly Thr Ala Gly
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic Peptide 25

<400> SEQUENCE: 25

His Leu Lys Gly Leu Thr Gly Thr Ala Gly Lys Ile Ser Ser Ile
1               5                   10                  15

<210> SEQ ID NO 26
<211> LENGTH: 15
<212> TYPE: PRT
<213> ORGANISM: Artificial Sequence
<220> FEATURE:
```

<223> OTHER INFORMATION: Synthetic Peptide 26

<400> SEQUENCE: 26

Thr Gly Thr Ala Gly Lys Ile Ser Ser Ile Ser Gln Pro Gly Asn
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Peptide 27

<400> SEQUENCE: 27

Lys Ile Ser Ser Ile Ser Gln Pro Gly Asn Asp Phe Ser Thr Lys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic Peptide 28

<400> SEQUENCE: 28

Ser Gln Pro Gly Asn Asp Phe Ser Thr Lys Asp Gly Asp Asn Asp
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic Peptide 29

<400> SEQUENCE: 29

Asp Phe Ser Thr Lys Asp Gly Asp Asn Asp Lys Cys Ile Cys Lys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic Peptide 30

<400> SEQUENCE: 30

Asp Gly Asp Asn Asp Lys Cys Ile Cys Lys Cys Ser Gln Met Leu
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide 31

<400> SEQUENCE: 31

Cys Ser Gln Met Leu Thr Gly Gly Trp Trp Phe Asp Ala Cys Gly
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic Peptide 32

```
<400> SEQUENCE: 32

Cys Ser Gln Met Leu Thr Gly Gly Trp Trp Phe Asp Ala Cys Gly
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic Peptide 33

<400> SEQUENCE: 33

Thr Gly Gly Trp Trp Phe Asp Ala Cys Gly Pro Ser Asn Leu Asn
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic Peptide 34

<400> SEQUENCE: 34

Phe Asp Ala Cys Gly Pro Ser Asn Leu Asn Gly Met Tyr Tyr Pro
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic Peptide 35

<400> SEQUENCE: 35

Pro Ser Asn Leu Asn Gly Met Tyr Tyr Pro Gln Arg Gln Asn Thr
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic Peptide 36

<400> SEQUENCE: 36

Gly Met Tyr Tyr Pro Gln Arg Gln Asn Thr Asn Lys Phe Asn Gly
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic Peptide 37

<400> SEQUENCE: 37

Gln Arg Gln Asn Thr Asn Lys Phe Asn Gly Ile Lys Trp Tyr Tyr
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic Peptide 38
```

<400> SEQUENCE: 38

Asn Lys Phe Asn Gly Ile Lys Trp Tyr Tyr Trp Lys Gly Ser Gly
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic Peptide 39

<400> SEQUENCE: 39

Ile Lys Trp Tyr Tyr Trp Lys Gly Ser Gly Tyr Ser Leu Lys Ala
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic Peptide 40

<400> SEQUENCE: 40

Trp Lys Gly Ser Gly Tyr Ser Leu Lys Ala Thr Thr Met Met Ile
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic Peptide 41

<400> SEQUENCE: 41

Tyr Ser Leu Lys Ala Thr Thr Met Met Ile Arg Pro Ala Asp Phe
1               5                   10                  15

<210> SEQ ID NO 42
<211> LENGTH: 496
<212> TYPE: PRT
<213> ORGANISM: Artificial Sequence
<220> FEATURE:
<223> OTHER INFORMATION: Human Ang2 protein

<400> SEQUENCE: 42

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
            35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp

```
            130                 135                 140
Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
            165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
            245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
            290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
            325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
            370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
            405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
            450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
            485                 490                 495

<210> SEQ ID NO 43
<211> LENGTH: 25
<212> TYPE: PRT
<213> ORGANISM: Artificial Sequence
<220> FEATURE:
<223> OTHER INFORMATION: Synthetic Ang2 fragment 1

<400> SEQUENCE: 43

Glu Tyr Trp Leu Gly Asn Glu Phe Val Ser Gln Leu Thr Asn Gln Gln
```

```
1               5                  10                 15
Arg Tyr Val Leu Lys Ile His Leu Lys
            20                 25

<210> SEQ ID NO 44
<211> LENGTH: 20
<212> TYPE: PRT
<213> ORGANISM: Artificial Sequence
<220> FEATURE:
<223> OTHER INFORMATION: Synthetic Ang2 fragment 2

<400> SEQUENCE: 44

His Thr Thr Asn Gly Ile Tyr Thr Leu Thr Phe Pro Asn Ser Thr Glu
1               5                   10                  15

Glu Ile Lys Ala
            20
```

PEPTIDE FOR INHIBITION OF BINDING BETWEEN ANGIOPOIETIN-2 AND INTEGRIN AND USE THEREOF

CROSS-REFERENCE TO RELATED APPLICATIONS

This application claims the benefit of Korean Patent Application No. 10-2012-0116155, filed on Oct. 18, 2012 in the Korean Intellectual Property Office, the entire disclosures of which are herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 15,318 Byte ASCII (Text) file named "713444_ST25(2).TXT" created on Jun. 22, 2015.

BACKGROUND

1. Field

Provided are angiopoietin-2 (Ang2) derived peptides, and a use of the peptides for inhibition of binding between Ang2 and integrin or prevention and/or treatment of a disease caused by the activation of Ang2 or the binding between Ang2 and integrin.

2. Description of the Related Art

Tie2 is a vascular endothelial cell surface receptor that binds angiopoietins, protein growth factors involved in the formation and maintenance of blood vessels. Angiopoietin-2 (Ang2), a Tie2 antagonist, competes with angiopoietin 1 (Ang1), a Tie2 agonist, to suppress signal transduction by Tie2. Thus, Ang2 inhibits the binding between Ang1 and Tie2, which maintains the stability of vascular endothelial cells. Consequently, Ang2 promotes angiogenesis through dynamic rearrangement of blood vessels.

Since angiogenesis is an essential element of cancer growth, cancers may be prevented or treated by suppressing angiogenesis through inhibition of the Tie2-dependent functions of Ang2. Indeed, various attempts to prevent the progression of cancers using Ang2 specific antibodies have been made.

Recently, it has been observed that Ang2 can not only induce the growth of cancers through Tie2-dependent angiogenesis, but can also promote the metastasis of cancers through a Tie2-independent mechanism. To inhibit the Ang2-mediated progression of cancers, it is important to suppress Ang2-Tie2 signaling. However, blocking a Tie2-independent signaling pathway (e.g., an Ang2-integrin signaling pathway) would also be desirable to enhance the efficacy of anti-cancer drugs. Thus, there remains a need for compositions and methods that can inhibit the Tie2-independent signaling pathway, such as the Ang2-integrin signaling pathway.

SUMMARY

An embodiment provides a peptide for inhibition of binding between Ang2 and integrin.

Another embodiment provides a polypeptide molecule containing the peptide for inhibition of binding between Ang2 and integrin, and a polypeptide complex containing the polypeptide molecule.

Another embodiment provides a composition for inhibition of binding between Ang2 and integrin, including at least one selected from the group consisting of a peptide for inhibition of binding between Ang2 and integrin, a polypeptide molecule containing the peptide, and a polypeptide complex containing the polypeptide molecule as an active ingredient.

Another embodiment provides a composition for prevention and/or treatment of a disease caused by the activation of Ang2 or the binding between Ang2 and integrin, including at least one selected from the group consisting of a peptide for inhibition of binding between Ang2 and integrin, a polypeptide molecule containing the peptide, and a polypeptide complex containing the polypeptide molecule as an active ingredient.

Another embodiment provides a method of inhibition of binding between Ang2 and integrin, including administering a therapeutically effective amount of at least one selected from the group consisting of a peptide for inhibition of binding between Ang2 and integrin, a polypeptide molecule containing the peptide, and a polypeptide complex containing the polypeptide molecule, to a patient who is in need of inhibition of binding between Ang2 and integrin.

Another embodiment provides a method of prevention and/or treatment of a disease caused by the activation of Ang2 or the binding between Ang2 and integrin, including administering a therapeutically effective amount of at least one selected from the group consisting of a peptide for inhibition of binding between Ang2 and integrin, a polypeptide molecule containing the peptide, and a polypeptide complex containing the polypeptide molecule, to a patient who is in need of prevention and/or treatment of diseases caused by the activation of Ang2 or the binding between Ang2 and integrin.

Another embodiment provides a method of developing a medicament for prevention and/or treatment of diseases caused by the activation of Ang2 or the binding between Ang2 and integrin, including combining a candidate substance with integrin and Ang2, or a reactant of integrin and Ang2, and determining whether the candidate substance inhibits binding between integrin and Ang2. The candidate substance is selected as a potential drug for prevention and/or treatment of diseases caused by the activation of Ang2 or the binding between Ang2 and integrin when the binding level between integrin and Ang2 is lower in the presence of the candidate substance than the binding level between integrin and Ang2 in the absence of the candidate substance.

Another embodiment provides a composition for detection of integrin, including at least one selected from the group consisting of a peptide for inhibition of binding between Ang2 and integrin, a polypeptide molecule containing the peptide, and a polypeptide complex containing the polypeptide molecule.

Another embodiment provides a method for detection of integrin, including treating a sample with at least one selected from the group consisting of a peptide for inhibition of binding between Ang2 and integrin, a polypeptide molecule containing the peptide, and a polypeptide complex containing the polypeptide molecule, and detecting the presence of a protein which binds to the peptide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is a fluorescence microscopy image that shows the morphological change of U87MG cells when bound to Ang2-coated surface.

FIG. 14 is a graph (left) and fluorescence images (right) showing the migration levels of U87MG cells when treated with Ang2 protein or its modified form (Q362A).

FIG. 17 is a graph that shows the effect of C-body on Ang2-integrin α5β1 binding on cell surface (top), and geometric means of Ang2 binding in cells expressing different quantities of GFP, which are plotted as larger red dots (bottom).

DETAILED DESCRIPTION

Figure 1:
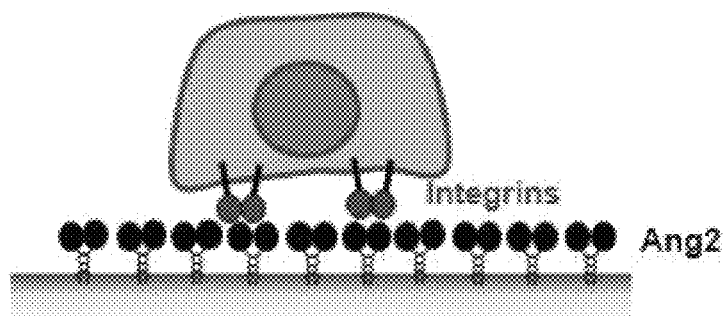
FIG. 1 is a schematic picture showing a cell adhesion assay design using human glioblastoma cell line (U87MG) which does not express Tie2.

The inhibition of Ang2-dependent adhesion of cells which do not express Tie2 means that there should be another receptor for Ang2 other than Tie2.

In accordance with one embodiment of the present invention, there is provided a leading substance capable of inhibiting Tie2-independent Ang2 functions by examining whether U87MG, a glioblastoma cancer cell line, which does not express Tie2, can adhere to surfaces coated with Ang2 in the presence of various peptides.

In order to verify the Tie2-independent Ang2 functions, the presence of a novel binding receptor of Ang2 other than Tie2 was confirmed through the following Example 1 where cells which do not express Tie2 adhered to an Ang2-coated surface. Example 3 shows that the novel binding receptor of Ang2 is integrin.

One embodiment of the present invention provides a use of integrin as a binding receptor of Ang2.

The Ang2 may originate from mammals including primates such as humans and monkeys, rodents such as mice and rats, and the like. For example, the Ang2 may be human Ang2 (e.g., NCBI Accession No. O15123 etc.), monkey Ang2 (e.g., NCBI Accession No. Q8MIK6 etc.), mouse Ang2 (e.g., NCBI Accession No. O35608 etc.), or rat Ang2 (e.g., NCBI Accession No. O35462 etc.), but is not limited thereto.

The integrin is a protein which mediates cell adhesion. The integrin has a heterodimer structure including an alpha (α) subunit and a beta (β) subunit. In mammals, 18 types of alpha subunits and 8 types of beta subunits have been identified. The integrins may originate from mammals including primates such as humans and monkeys, and rodents such as mice and rats. For example, the integrins may be human integrins, monkey integrins, mouse integrins, or rat integrins, but are not limited thereto. In each species, 24 types of integrins and their amino acid sequences have been identified, and are well known in the art to which the invention pertains. For instance, the integrins may be human integrins, and the integrin types thereof may include alpha5beta1 (α5β1) (α5: NCBI Accession No. P08648, β1: NCBI Accession No. P05556), alphaVbeta1 (αVβ1) (αV: NCBI Accession No. P06756, β1: NCBI Accession No. P05556), and alphaVbeta3 (αVβ3) (αV: NCBI Accession No. P06756, β3: NCBI Accession No. P05106), but are not limited thereto.

Another embodiment provides peptides for inhibition of binding between Ang2 and integrin.

The peptides for inhibition of binding between Ang2 and integrin may originate from a portion of the receptor binding domain (RBD) of the Ang2 protein, which is involved with binding to receptors such as Tie2. For instance, the peptides may be those including, consisting essentially of, or consisting of 5 to 50 consecutive amino acids, particularly 5 to 30 consecutive amino acids, and more particularly 5 to 15 consecutive amino acids of the RBD of the Ang2 protein, wherein the Ang2 protein may be the protein of NCBI Accession No. O15123 (SEQ ID No. 42), and the like. The RBD may correspond to the amino acids from $282^{nd}$ to $496^{th}$ positions of the Ang2 protein of SEQ ID No. 42. The peptides may be fragments of Ang2 protein that do not exhibit the pro-angiogenic properties of Ang2.

Without wishing to be bound by any particular theory or mechanism, the peptides are believed to inhibit the binding of Ang2 and integrin by competing with Ang2 for binding with integrins.

By way of further example, Table 1 provides 41 peptide sequences each with 15 consecutive amino acids of the RBD (amino acids from $282^{nd}$ to $496^{th}$ positions) of the Ang2 protein (NCBI Accession No. O15123; SEQ ID No. 42). The peptides were prepared such that 10 amino acids overlap between neighboring peptides (see Table 1).

TABLE 1

| SEQ ID NO. | Amino acid sequences of peptides |
|---|---|
| 1 | RDCAE VFKSG HTTNG |
| 2 | VFKSG HTTNG IYTLT |
| 3 | HTTNG IYTLT FPNST |
| 4 | IYTLT FPNST EEIKA |
| 5 | FPNST EEIKA YCDME |
| 6 | EEIKA YCDME AGGGG |
| 7 | YCDME AGGGG WTIIQ |
| 8 | AGGGG WTIIQ RREDG |
| 9 | WTIIQ RREDG SVDFQ |
| 10 | RREDG SVDFQ RTWKE |
| 11 | SVDFQ RTWKE YKVGF |
| 12 | RTWKE YKVGF GNPSG |
| 13 | YKVGF GNPSG EYWLG |
| 14 | GNPSG EYWLG NEFVS |
| 15 | EYWLG NEFVS QLTNQ |
| 16 | NEFVS QLTNQ QRYVL |
| 17 | QLTNQ QRYVL KIHLK |
| 18 | QRYVL KIHLK DWEGN |
| 19 | KIHLK DWEGN EAYSL |
| 20 | DWEGN EAYSL YEHFY |
| 21 | EAYSL YEHFY LSSEE |
| 22 | YEHFY LSSEE LNYRI |
| 23 | LSSEE LNYRI HLKGL |
| 24 | LNYRI HLKGL TGTAG |
| 25 | HLKGL TGTAG KISSI |
| 26 | TGTAG KISSI SQPGN |
| 27 | KISSI SQPGN DFSTK |
| 28 | SQPGN DFSTK DGDND |
| 29 | DFSTK DGDND KCICK |
| 30 | DGDND KCICK CSQML |
| 31 | KCICK CSQML TGGWW |
| 32 | CSQML TGGWW FDACG |
| 33 | TGGWW FDACG PSNLN |
| 34 | FDACG PSNLN GMYYP |
| 35 | PSNLN GMYYP QRQNT |
| 36 | GMYYP QRQNT NKFNG |

TABLE 1-continued

| SEQ ID NO. | Amino acid sequences of peptides |
|---|---|
| 37 | QRQNT NKFNG IKWYY |
| 38 | NKFNG IKWYY WKGSG |
| 39 | IKWYY WKGSG YSLKA |
| 40 | WKGSG YSLKA TTMMI |
| 41 | YSLKA TTMMI RPADF |

Figure 10:
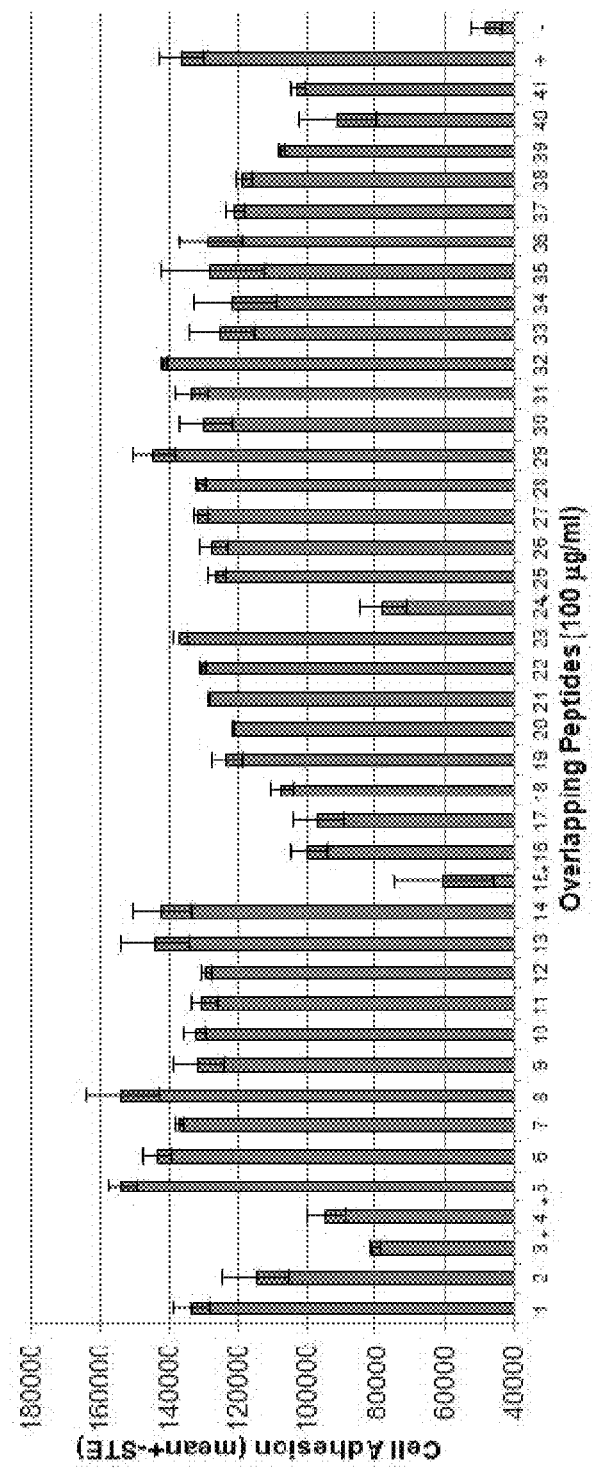
FIG. 10 is a graph showing the effects of 41 Ang2-derived peptides (FIG. 9) on U87MG cell adhesion to Ang2-coated wells.

Of these 41 peptides, peptides containing the amino acid sequences of SEQ ID Nos. 3, 4, 15, 16, 17, 24 and 40 show remarkably high inhibition activity against the binding of Ang2 and integrin (see FIG. 10). The peptides of SEQ ID Nos. 15 to 17 show excellent integrin-Ang2 binding inhibition activity. SEQ ID Nos. 15 to 17 are peptides adjacent to each other, of which 10 amino acids are overlapped. They are designed so that they include consecutive 15 amino acids of the amino acid sequence of SEQ ID No. 43 (EYWLGNEFVSQLTNQQRYVLKIHLK) and 10 amino acids thereof are overlapped with the adjacent peptide. The $11^{th}$ to $15^{th}$ amino acids of SEQ ID No. 43 correspond to the $362^{nd}$ to $366^{th}$ amino acids of the Ang2 protein, and correspond to side chains exposed to the outside of a three-dimensional structure of Ang2 protein and thus have excellent binding activity to integrins. Moreover, as shown in FIG. 11 to FIG. 14, in particular, the $11^{th}$ amino acid (Q) of SEQ ID No. 43 (corresponding to $362^{nd}$ amino acid of Ang2 protein (SEQ ID No. 42)) has a crucial role in binding to integrins and the resultant cell invasion. Accordingly, the peptides for inhibition of binding between Ang2 and integrin may be those including 5 to 25 consecutive amino acids, particularly 5 to 20 consecutive amino acids, and more particularly 5 to 15 consecutive amino acids, essentially containing the $11^{th}$ amino acid or amino acids from $11^{th}$ to $15^{th}$ positions of SEQ ID No. 43.

The peptides of SEQ ID Nos. 3 and 4 are also peptides showing excellent integrin-Ang2 binding inhibition activity and they are adjacent to each other, of which 10 amino acids are overlapped. They are designed so that 10 amino acids of the amino acid sequences of SEQ ID No. 44 (HTTNGIYTLT-FPNSTEEIKA) are overlapped and they include 15 consecutive amino acids within the amino acid sequence of SEQ ID No. 44. In light of the excellent integrin-Ang2 binding inhibition activity of the peptides of SEQ ID Nos. 3 and 4, the inclusion of a part or whole of 10 amino acids of SEQ ID No. 44 (underlined), which are overlapped in SEQ ID Nos. 3 and 4, may result in integrin-Ang2 binding inhibition activity. Accordingly, the peptides for inhibition of binding between Ang2 and integrin may be those including 11 to 20 consecutive amino acids, particularly 11 to 15 consecutive amino acids of the amino acid sequence of SEQ ID No. 44. For example, the peptides may be those including 11 to 20 consecutive amino acids, particularly 11 to 15 consecutive amino acids, essentially containing amino acids from $6^{th}$ to $15^{th}$ positions of SEQ ID No. 44.

Therefore, the peptide for inhibition of binding between Ang2 and integrin may be at least one selected from the group consisting of:

a peptide including or consisting essentially of 5 to 25 consecutive amino acids within the amino acid sequence of SEQ ID No. 43, containing amino acid at position 11 or amino acids from $11^{th}$ to $15^{th}$ positions of SEQ ID No. 43 (e.g., peptides containing the amino acid sequences of SEQ ID No. 15, SEQ ID No. 16, or SEQ ID No. 17), a peptide including or consisting essentially of 11 to 20 consecutive amino acids within the amino acid sequence of SEQ ID No. 44, containing amino acids 6 to 15 of SEQ ID No. 44 (e.g., peptides containing the amino acid sequences of SEQ ID No. 3 or SEQ ID No. 4), a peptide containing or consisting essentially of the amino acid sequence of SEQ ID No. 24, and a peptide containing or consisting essentially of the amino acid sequence of SEQ ID No. 40.

In one embodiment, the peptide for inhibition of binding between Ang2 and integrin may be at least one peptide selected from the group consisting of a peptide containing the amino acid sequence of SEQ ID No. 15, a peptide containing the amino acid sequence of SEQ ID No. 3, a peptide containing the amino acid sequence of SEQ ID No. 24, a peptide containing the amino acid sequence of SEQ ID No. 4, a peptide containing the amino acid sequence of SEQ ID No. 40, a peptide containing the amino acid sequence of SEQ ID No. 16, and a peptide containing the amino acid sequence of SEQ ID No. 17.

In another embodiment, there is provided a polypeptide molecule having a certain structure, wherein the peptide for inhibition of binding between Ang2 and integrin is linked to other peptide(s).

For example, the polypeptide molecule may have a first peptide and a second peptide, wherein the first peptide may be a peptide for inhibition of binding between Ang2 and integrin, that is, at least one peptide selected from the group consisting of a peptide including or consisting essentially of 5 to 25 consecutive amino acids within the amino acid sequence of SEQ ID No. 43 (EYWLGNEFVSQLTNQQRYVLKIHLK), containing amino acid at position 11 or amino acids from $11^{th}$ to $15^{th}$ positions of SEQ ID No. 43; a peptide including or consisting essentially of 11 to 20 consecutive amino acids within the amino acid sequence of SEQ ID No. 44 (HTT-NGIYTLTFPNSTEEIKA), containing amino acids $6^{th}$ to $15^{th}$ positions of SEQ ID No. 44; a peptide containing or consisting essentially of the amino acid sequence of SEQ ID No. 24; and a peptide containing or consisting essentially of the amino acid sequence of SEQ ID No. 40; or a peptide repeat where the at least one peptide is repeated (e.g., 2 to 20 times, particularly 2 to 10 times, and more particularly 2 to 5 times) with or without the linker; and the second peptide may be selected from the group consisting of a heavy chain or light chain of an antibody, a constant region of the heavy chain or light chain of an antibody, and an Fc fragment of an antibody.

The second peptide is a peptide that functions to maintain or support the structure of the polypeptide molecule. The second peptide may be an antibody or a part thereof, for example, selected from the group consisting of a heavy chain or light chain of an antibody, a constant region of the heavy chain or light chain of the antibody, and an Fc fragment of the antibody. The constant region of the heavy chain or light chain or Fc fragment of an antibody refer to, without any particular restrictions, a constant region or Fc region of an ordinary antibody, and for example, may be a constant region or Fc fragment of all the iso types of human immunoglobulins (e.g., IgA, IgD, IgG, IgE, and IgM).

The polypeptide molecule may further include a linker. The linker may function in coupling the first peptide and the second peptide. In case that the first peptide is a peptide repeat, the linker may function in coupling two or more repeated peptides within the peptide repeat. The linker may be a peptide consisting of 2 to 20 amino acids, for example, 3 to 10 amino acids. For example, the linker may have the amino acid sequences of $G_m S_n$ (m and n refer to the number of amino acids G and S and are each independently an integer of 1 to 10, for example, an integer of 1 to 5), but is not limited thereto.

The polypeptide molecule may have a structure where the first peptide (i.e., a peptide for inhibition of binding between Ang2 and integrin or a repeat of the peptide) is coupled to either the N terminus, or the C terminus, of the second peptide. When more than one first peptide is used, the first peptides may, optionally, be tandomly coupled to the N terminus or the C terminus of the second peptide (e.g., a heavy chain or light chain of an antibody, a constant region of the heavy chain or light chain of the antibody, or an Fc fragment of the antibody) with the linker or without the linker. Additionally, when two first peptides are used, one may be coupled to the N terminus of the second peptide and one may be coupled to the C terminus of the second peptide.

In another embodiment, there is provided a polypeptide complex containing 2 or more, for example, 2 to 4 of the polypeptide molecules. The polypeptide complex may be those having a multimer structure by combination of 2 or more, for example, 2 to 4 of the polypeptide molecules. The first peptides and the second peptides included in two or more polypeptide molecules within a polypeptide complex may be the same with or different from each other. In the polypeptide complex, the polypeptide molecules may form a multimer structure by being combined at the second peptide region (e.g., an Fc fragment region).

As the polypeptide molecule and the polypeptide complex include the first peptide, that is the peptide for inhibition of binding between Ang2 and integrin or the repeat thereof, which plays a role similar to complementarity determining regions (CDR) and the second peptides with structural functions (e.g., a heavy chain or light chain of an antibody, a constant region of the heavy chain or light chain of the antibody, and an Fc fragment of the antibody), they have a structure similar to an antibody and thus, are referred to as "peptibody" herein.

Figure 15:
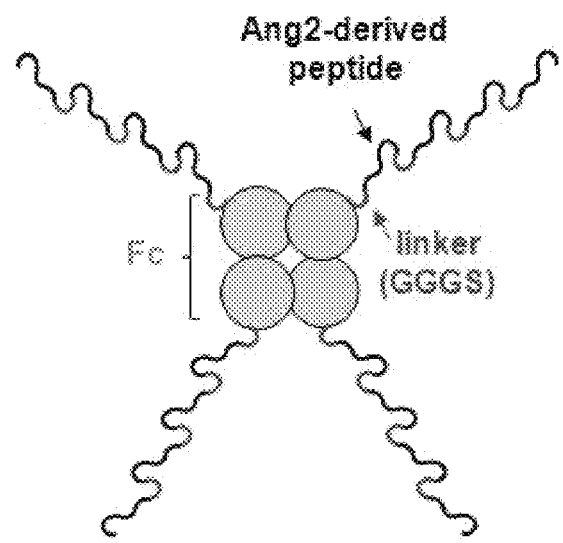
FIG. 15 is a schematic diagram showing the structure of a peptibody (C-body) according to one embodiment.

In one embodiment, the peptibody may have a structure as shown in FIG. 15. The construct of FIG. 15 has a structure having two polypeptide molecules, wherein each polypeptide molecule has two peptide repeats and a Fc fragment; two peptide repeats are attached to both of the C terminus and the N terminus of the Fc fragment via a linker (e.g., GGGS)(SEQ ID NO:45); the two polypeptide molecules are coupled at the Fc fragments; and each peptide repeat has 4 peptides for inhibition of binding between Ang2 and integrin. The 4 peptides are linked via three linkers (e.g., GGGS)(SEQ ID NO: 45).

Not only the peptides for inhibition of binding between Ang2 and integrin, but also the peptibody containing them (polypeptide molecules or polypeptide complexes) inhibits binding between Ang2 and integrin significantly (see FIG. 16 to FIG. 22).

Where the second peptide which performs structural functions within the polypeptide molecule or the polypeptide complex is a heavy chain and/or a light chain of an antibody including its intrinsic CDR, the polypeptide molecule or the polypeptide complex may further exhibit antigen-specific effects which are intrinsically possessed by the antibody, in addition to Ang2-integrin binding inhibition effects.

Therefore, the peptide for inhibition of binding between Ang2 and integrin, the polypeptide molecule containing the peptides, and/or the polypeptide complex containing the polypeptide molecules have excellent activity of inhibiting the binding between Ang2 and integrin and accordingly, they have excellent prevention and/or treatment effects against diseases (e.g., cancers, cancer metastasis, eye diseases, and inflammatory diseases) induced by Ang2 activation and/or binding between Ang2 and integrin.

Another embodiment provides a pharmaceutical composition for inhibition of binding between Ang2 and integrin, including at least one selected from the group consisting of a peptide for inhibition of binding between Ang2 and integrin, a polypeptide molecule containing the peptide, and a polypeptide complex containing the polypeptide molecule as an active ingredient. In another embodiment, there is provided a method for inhibition of binding between Ang2 and integrin, including administering a therapeutically effective amount of at least one selected from the group consisting of a peptide for inhibition of binding between Ang2 and integrin, a polypeptide molecule containing the peptide, and a polypeptide complex containing the polypeptide molecule, to a patient in need of inhibition of binding between Ang2 and integrin. This method may further include a step of identifying a patient who is in need of inhibition of binding between Ang2 and integrin, prior to the administration step. In another embodiment, there is provided a use of at least one selected from the group consisting of a peptide for inhibition of binding between Ang2 and integrin, a polypeptide molecule containing the peptide, and a polypeptide complex containing the polypeptide molecule, for inhibition of binding between Ang2 and integrin, or a use for the preparation of a composition for inhibition of binding between Ang2 and integrin.

Still another embodiment provides a pharmaceutical composition for prevention and/or treatment of diseases caused by the activation of Ang2 or the binding between Ang2 and integrin, including at least one selected from the group consisting of a peptide for inhibition of binding between Ang2 and integrin, a polypeptide molecule containing the peptide, and a polypeptide complex containing the polypeptide molecule as an active ingredient. In another embodiment, there is provided a method for prevention and/or treatment of diseases caused by the activation of Ang2 or the binding between Ang2 and integrin, including administering a therapeutically effective amount of at least one selected from the group consisting of a peptide for inhibition of binding between Ang2 and integrin, a polypeptide molecule containing the peptide, and a polypeptide complex containing the polypeptide molecule, to a patient in need of prevention and/or treatment of diseases caused by the activation of Ang2 or the binding between Ang2 and integrin. This method may further include a step of identifying a patient who is in need of prevention and/or treatment of cancer and/or cancer metastasis, prior to the administration step. In another embodiment, there is provided a use of at least one selected from the group consisting of a peptide for inhibition of binding between Ang2 and integrin, a polypeptide molecule containing the peptide, and a polypeptide complex containing the polypeptide molecule, for prevention and/or treatment of diseases caused by the activation of Ang2 or the binding between Ang2 and integrin, or a use for the preparation of a composition for prevention and/or treatment of diseases caused by the activation of Ang2 or the binding between Ang2 and integrin.

The pharmaceutical compositions may further include pharmaceutically acceptable carriers including, but are not limited to, at least one selected from the group consisting of lactose, dextrose, sucrose, sorbitol, mannitol, starches, gum acacia, calcium phosphate, alginates, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc. Furthermore, the pharmaceutical compositions may further include at least one selected from the group consisting of a diluent, excipient, lubricating agent, wetting agent, sweetening agent, flavoring agent, emulsifying agent, preserving agent and so on.

The pharmaceutical compositions may be administered orally or parenterally. Parenteral administration may be performed by intravenous injection, subcutaneous injection, muscular injection, intraperitoneal injection, endothelial administration, local administration, intranasal administration, intrapulmonary administration, or rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

A dosage of an active ingredient in the pharmaceutical compositions may be prescribed in a variety of ways, depending on factors including formulation methods, administration manners, ages of patients, body weight, gender, pathologic conditions, diets, administration time, administration interval, administration route, excretion speed, and reaction sensitivity. For example, a daily dose of the pharmaceutical compositions may be in ranges of 0.001 to 1000 mg/kg, particularly 0.01 to 100 mg/kg, and more particularly 0.1 to 50 mg/kg based on the active ingredient, but not limited thereto. The daily dose may be formulated into a single formulation in a unit dosage form or formulated in suitably divided dosage forms, or it may be manufactured to be contained in a multiple dosage container. The therapeutically effective amount or pharmaceutically effective amount refers to such a dose that the active ingredient can exhibit a desired activity, that is, inhibition activity of binding between Ang2 and integrin or prevention and/or treatment activity of cancer and/or cancer metastasis.

The pharmaceutical compositions may be a solution in oil or an aqueous medium, a suspension, syrup or an emulsifying solution form, or formulated into a form of an extract, powders, granules, a tablet or a capsule, and they may further include a dispersing agent or a stabilizing agent for the formulation thereof.

The diseases caused by the activation of Ang2 or the binding between Ang2 and integrin may be cancers, cancer metastasis, eye diseases such as macular degeneration (e.g., age-related macular degeneration), and inflammatory diseases such as septicemia, psoriasis, and acute organ failure.

The cancers may include all kinds of cancers induced or promoted by binding between Ang2 and integrin and for instance, they may be solid cancers. Specifically, the cancers may be squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, pancreatic cancer, glioblastoma, cervical cancer, ovarian cancer, liver cancer, bladder cancer, breast cancer, colon cancer, large intestine cancer, endometrial carcinoma or uterine carcinoma, salivary gland tumor, kidney cancer, prostate cancer, vulvar cancer, thyroid cancer, head and neck cancers, brain cancer and osteosarcoma, but are not limited thereto.

Another embodiment provides a method of screening a candidate substance for inhibition of the binding between Ang2 and integrin or for prevention and/or treatment of diseases caused by the activation of Ang2 or binding between Ang2 and integrin (e.g., cancers and/or cancer metastasis), employing a use of integrin as an Ang2 binding receptor.

The method of screening may include: preparing an integrin-expressing cell or an integrin-coated surface; treating the cell or the surface with angiopoietin (Ang2) to form a reacted product; treating a part of the reacted product with a test substance; and measuring binding levels between Ang2 and integrin in the part of the reacted product treated with the test substance and in the part of the reacted product not treated with the test substance.

In another embodiment, the screening method may include: preparing an angiopoietin2 (Ang2)-coated surface; treating the surface with integrin-expressing cells or integrin to form a reacted product; treating a part of the reacted product with a test substance; and measuring binding levels between Ang2 and integrin in the part of the reacted product which is treated with the test substance and in a part of the reacted product which is not treated with the test substance.

In the above screening method, the test substance may be determined to be a candidate substance for inhibition of the binding between Ang2 and integrin or for prevention or treatment of diseases caused by the activation of Ang2 or the binding between Ang2 and integrin when the binding level between Ang2 and integrin in the part of the reacted product treated with the test substance is lower than that in the part of the reacted product which is not treated with the test substance.

The test substance may be at least one selected from the group consisting of a variety of artificially synthesized or natural compounds, antibody, polypeptides, oligopeptides, polynucleotides, oligonucleotides, anti sense-RNA, short hairpin RNA (shRNA), small interference RNA (siRNA), aptamers, and natural substance extracts.

The binding level between Ang2 and integrin may be measured by any ordinary methods, for example, by flow cytometry or ELISA methods, but is not limited thereto.

The surfaces coated with integrin or Ang2 may be, without any particular restrictions, any surfaces capable of being coated by proteins, and they may be selected from all kinds of solid or semi-solid surfaces, including plastics, glass, metals, polymer resins, and the like.

According to another embodiment, there is provided a composition for detection of integrin, including at least one selected from the group consisting of a peptide for inhibition of binding between Ang2 and integrin, a polypeptide molecule containing the peptide, and a polypeptide complex containing the polypeptide molecule. There is provided in still another embodiment a method for detection of integrin, including treating a specimen with at least one selected from the group consisting of a peptide for inhibition of binding between Ang2 and integrin, a polypeptide molecule containing the peptide, and a polypeptide complex containing the polypeptide molecule, and detecting the presence of a protein which binds to the peptides.

The specimen may be cells, tissues, body fluids, or other protein mixtures. The presence of a protein which binds to the peptides may be measured by any ordinary protein-peptide binding detection methods, for example by flow cytometry or ELISA methods.

Another embodiment provides a method of developing a drug for prevention or treatment of diseases caused by the activation of Ang2 or binding between Ang2 and integrin including: a step of preparing integrin-expressing cells or an angiopoietin-2 (Ang2) coated surface; a step of treating the cell or the surface with integrin surface-expressing cells or integrin to be reacted; a step of treating a part of the reacted product with a test substance; and a step of measuring binding levels between Ang2 and integrin in the part of the reacted product treated with the test substance and in a part of the reacted product which is not treated with the test substance, wherein the test substance is determined to be a drug for prevention or treatment of diseases caused by the activation of Ang2 or binding between Ang2 and integrin, when the binding level between Ang2 and integrin in the part of the reacted product treated with the test substance is lower than that in the part of the reacted product which is not treated with the test substance, and the diseases caused by the activation of Ang2 or the binding between Ang2 and integrin are selected from the group consisting of cancer, cancer metastasis, eye diseases, and inflammatory diseases.

The peptides capable of effectively blocking binding between Ang2 and integrin proposed in this invention exhibit treatment effects on diseases caused by the activation of Ang2 or the binding between Ang2 and integrin, for example, effective inhibition of not only the migration/invasion/metastasis of cancer cells but also the migration/invasion of vascular endothelial cells, by inhibiting the binding between Ang2 and integrin. Moreover, as the peptides may be combined with other biologics in a fusion form, the effects of the peptides may be combined with the effects of the other biologics to treat cancers or other diseases.

Hereafter, the present invention will be described in more detail through examples. The following examples are intended merely to illustrate one or more embodiments and are not construed to restrict the scope of the invention.

EXAMPLES

Example 1

Ang2 Dependent Cell Adhesion in Brain Cancer Cell Line (U87MG) Where Tie2 is not Expressed 1.1. Ang2 Dependent Cell Adhesion in U87MG Using a U87MG cell line which has been known to express integrin but not to express Tie2, angiopoietin-2 (hereafter, Ang2), dependent cell adhesion was tested and, as a result, it was verified that Ang2 could bind to receptors other than Tie2 (see FIG. 1).

A 96-well plate was treated with 100 μl of a solution obtained by diluting Ang2 (R&D systems; 623-AN-025/CF) in a phosphate buffered saline (PBS) at a concentration of 10 μg/ml and incubated at 4° C. for 16 hours so that the wells were coated with Ang2. Thereafter, the Ang2-coated 96 wells were washed twice with PBS, treated with 200 μl of PBS containing 2% (v/v) bovine serum albumin (BSA) and then incubated at a room temperature for 2 hours for blocking. For a negative control, wells that were blocked without Ang2 coating (i.e., treated with BSA only) were prepared.

During the blocking procedures, brain cancer cell line U87MG (ATCC, HTB-14™) which showed confluency of about 70-80% in a T75 flask was detached by trypsinization, washed twice with serum-free media (IMDA, invitrogen), and re-suspended in 10 ml of serum-free media at a concentration of about $3 \times 10^5$ cells/ml. 150 μl of the thus obtained cell suspension was added to each well of the 96-well plate that was prepared by performing coating and blocking procedures and incubating the plate in a $CO_2$ incubator at 37° C. for 2 hours to induce cell adhesion.

Then, the plate was washed 4 times with serum-free media that was warmed to 37° C. to remove cells that were not adhered. The adhesion level of cells was quantified by adding 200 μl of CellTiter-Glo reagent (Promega) diluted in IMDM at 1:1 and then, measuring luminescence at EnVision® Multilabel Reader (PerkinElmer) after 10 min.

Figure 2:
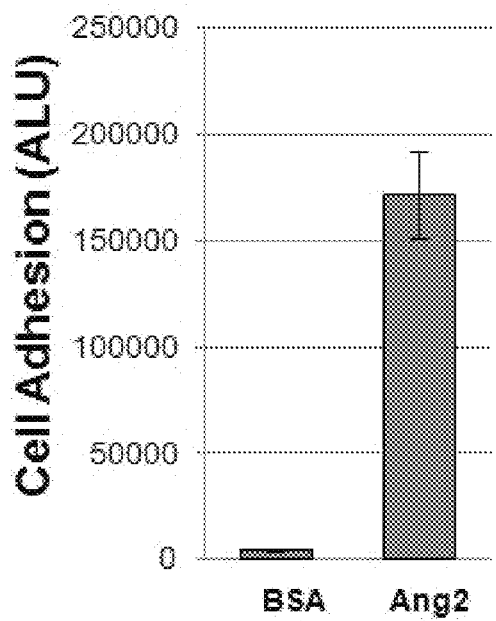
FIG. 2 is a graph showing the adhesion level of U87MG on Ang2-coated wells (ALU: arbitrary light unit).

The results are shown in FIG. 2. As seen in FIG. 2, whereas U87MG cell adhesion hardly occurred in the wells treated with only BSA which was prepared as the negative control, U87MG cell adhesion occurred in the wells with Ang2 adhered thereon in a significantly high level.

1.2. Presence or Absence of Tie2 Expression in U87MG

It was verified whether Tie2 was actually expressed or not in the U87MG cell line used in Example 1.1 above. For this, the proteins of the U87MG cell line (ATCC, HTB-14™) were developed using a sodium dodecyl sulfate-polyacrylamide gel electrophoresis (SDS-PAGE) experimental method, transferred to a nitrocellulose paper and then, treated with an antibody against Tie2 (santa cruz biotechnology, SC-324) to perform a western blotting method. Human umbilical vein endothelial cell line (HUVEC; ATCC, CRL-1730™), which has been well known to express Tie2, was used as a positive control. GAPDH was used as a control for the quantity of the total proteins to be loaded on gels.

Figure 3:
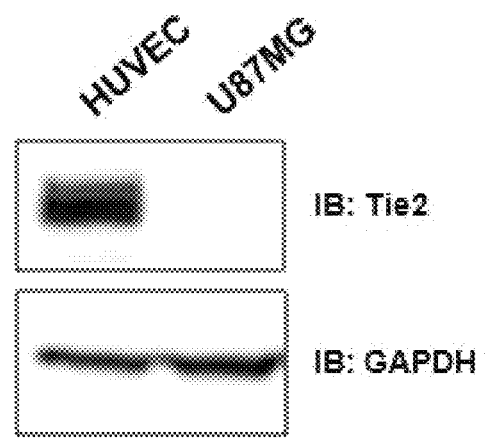
FIG. 3 is a western blot image showing whether Tie2 is expressed or not in U87MG cell line.

The thus obtained results are shown in FIG. 3. As seen in FIG. 3, U87MG cell line did not express Tie2.

Example 2

Morphology Change of U87MG Cells by Binding of Ang2

In order to observe morphology change of cells by Ang2, each well of μ-slide 8 well (ibidi GmbH) was coated using 100 μg/ml of poly-L-lysine (Sigma-Aldrich), 10 μg/ml of fibronectin (Sigma-Aldrich), or 10 μg/ml of Ang2 (R&D systems) in accordance with the method of Example 1.1, blocked with 2% BSA, followed by the addition of 150 μl of U87MG cell suspension, which was prepared in the same manner as in Example 1.1 above, and then incubated in a $CO_2$ incubator at 37° C. for 2 hours. Thereafter, it was washed 4 times with serum-free media that was warmed to 37° C. to remove cells that were not adhered, and the adhered cells were fixed by the addition of 4% formaldehyde and incubated at room temperature for 15 min. Using adhered rhodamine-phalloidin (Life Technologies) and DAPI (4',6-diamidino-2-phenylindole, Sigma-Aldrich), fibrous actin (f-actin, green) and nucleus (red), the cells were dyed and then observed through a fluorescence microscope.

The thus obtained results are shown in FIG. 4. Unlike the case coated with poly-L-lysine which simply attaches cells by electrical force, it was observed in the case coated with Ang2 that there were a lot of radically, sharply projected areas where f-actin is present in a condensed form. This is a unique structure which is distinguished from stress fiber or focal adhesion observed when coated with fibronectin which has been known as a typical ligand of integrins, and it suggests that the binding of Ang2 and integrin can facilitate invasion into other tissues by inducing the projection of cell membranes in f-actin dependent way.

Example 3

Binding Between Ang2 and Integrin (In Vitro)

After an ELISA plate was coated with diluents obtained by diluting 3 kinds of integrin proteins (alpha5beta1 ($\alpha5\beta1$; $\alpha5$: NCBI Accession No. P08648, β1: NCBI Accession No. P05556), alphaVbeta1 ($\alpha V\beta1$; αV: NCBI Accession No. P06756, β1: NCBI Accession No. P05556), and alphaVbeta3 ($\alpha V\beta3$; αV: NCBI Accession No. P06756, β3: NCBI Accession No. P05106); R&D systems)) in PBS at a concentration of 5 μg/ml (18 hours, 4° C.), it was blocked with 1% (v/v) BSA at a room temperature for 2 hours. Thereafter, it was treated with Ang2 protein having FLAG sequences (DYKD-DDDK, Sigma) tagged at its N-terminal (FLAG-Ang2, 0.1 ml of Ang2 protein solution diluted in PBS at a concentration of 10 μg/ml), incubated at a room temperature for 2 hours, and washed 5 times with PBS-t (0.1% (v/v) triton X-100 in PBS). Then, it was followed by the addition of anti-FLAG antibody (Sigma) conjugated with horse radish peroxidase (HRP) and washed 5 times with PBS-t. Binding between Ang2 and 3 kinds of the integrins was verified indirectly by measuring the quantity of anti-FLAG antibody remaining in the ELISA plate through color development reaction using TMB (3,3,5, 5-tetramethylbenzidine) as a substrate of HRP. As a negative control, one plate which was blocked without Ang2 protein treatment (BSA treatment only) was used.

Figure 5:
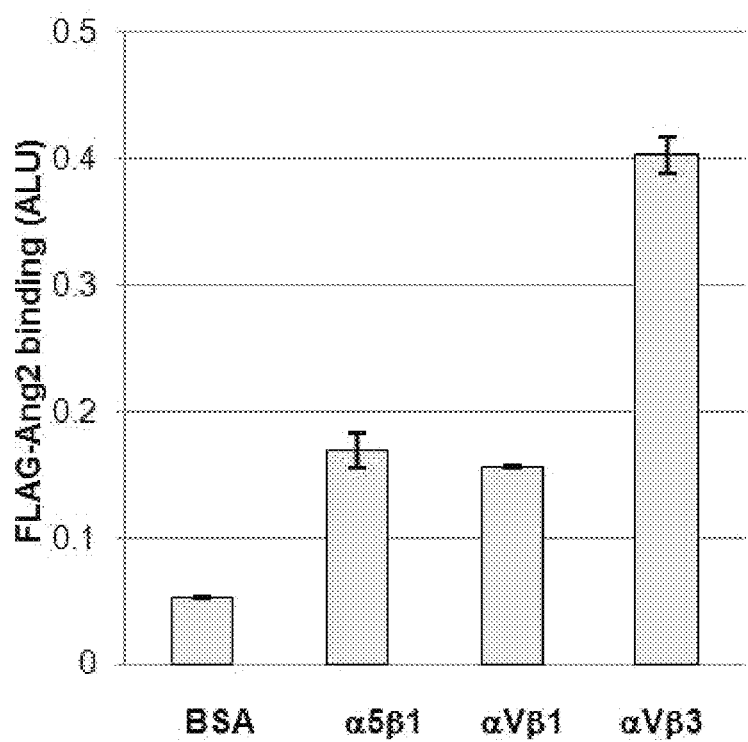
FIG. 5 is a graph showing an in vitro binding level of FLAG-tagged Ang2 (FLAG-Ang2) to integrin, measured by enzyme-linked immunosorbent assay (ELISA).

The results were shown in FIG. 5. As seen in FIG. 5, Ang2 proteins were revealed to bind to all 3 kinds of the integrins.

Example 4

Binding Between Ang2 and Integrin at Cell Membrane cDNA pairs of each integrin ($\alpha5\beta1$, $\alpha V\beta1$, and $\alpha V\beta3$) and cDNA (pTRACER™-CMV2, Invitrogen) encoding green fluorescent protein (GFP) as a transfection marker were transfected into Chinese Hamster Ovary (CHO) cell line (Korea Research Institute of Bioscience and Biotechnology, Biological Resource Center) using lipofectamine 2000 reagent (Invitrogen) pursuant to the manufacturer's recommended experimental procedures. Each cDNA (integrin α5, αV, β1, β3 4 kinds) used for transfection was purchased from Origene, with the corresponding open reading frame amplified using polymerase chain reaction, and cloned into pcDNA3.1 (+)/myc-His A (invitrogen).

The transfected cells were cultured under normal cell cultivation conditions (IMDM media containing 10% fetal bovine serum and penicillin/streptomycin at 10%, $CO_2$ incubator at 37° C.) for 24 hours.

Then, the cells were detached according to Example 1.1 above, re-suspended in serum-free media (IMDM) at about $2\times10^7$ cells/ml, and incubated at 4° C. for 1 hour after 45 μl of the cell solution was mixed with 5 ml of FLAG-Ang2 diluted in PBS at a concentration of 200 μg/ml. After the cells were fixed using 3% (v/v) formaldehyde and washed with IMDM, they were dyed with anti-FLAG antibody (Sigma) conjugated with R-phycoerythrin and then analyzed using flow cytometry.

Figure 6:
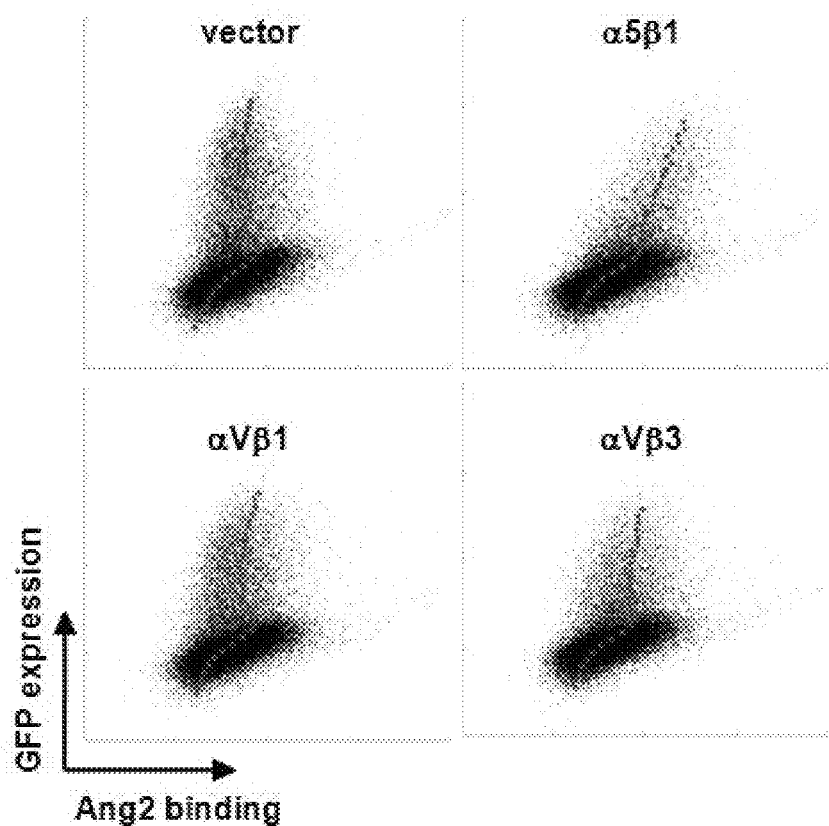
FIG. 6 shows dot plots which represent binding of FLAG-Ang2 to integrin on cell membranes. The Y axis represents the expression of GFP which is used as a transfection marker, the X axis shows the binding level of Ang2, and the red dot represents an average of the Ang2 binding levels in cells expressing different quantities of GFP.
Figure 7:
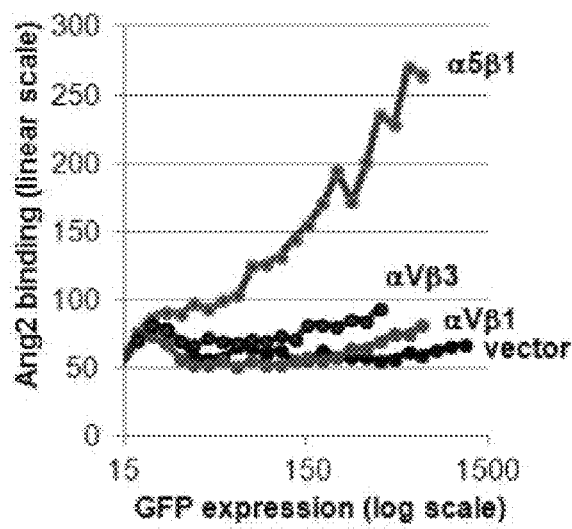
FIG. 7 is a graph of linear-log scale that shows the results of FIG. 6.

The results are shown in FIG. 6 and FIG. 7. In the dot plot of FIG. 6, the y axis represents the expression of GFP which is a transfection marker, and the x axis represents the Ang2 binding level. The bold dots represent an average of binding levels between integrin and Ang2 in several cells. As the slope of lines made of red dots in top parts of each graph decreases, binding level with Ang2 increases. In order to clearly show the Ang2 binding levels shown in FIG. 6, the red dots in FIG. 6 were converted into linear-log scales, which are shown in FIG. 7. It is seen from FIG. 7 that Ang2 bound to 3 kinds of the integrins at cell membranes and, in particular, that Ang2 bound especially well to $\alpha5\beta1$. On the contrary, in cells transfected only with vectors (with no integrins) used as a negative control, binding with integrin was irrelevant to GFP expression. Ang2 showed specific binding to the expressed integrin.

Example 5

Preparation of Ang2 Derived Peptides and Inhibition of Binding Between Ang2 and Integrin by the Peptides

5.1. Preparation of Ang2 Derived Peptides

Peptides were designed based on the receptor binding domain (RBD) of Ang2 protein (O15123; SEQ ID No. 42), which is involved with binding to Tie2. More particularly, a total of 41 peptides were designed so that they have 15 consecutive amino acids within amino acids 282 to 496 of the Ang2 protein of SEQ ID No. 42, wherein 10 amino acids are overlapped with neighboring peptides. The amino acid sequences of these peptides are shown in Table 2 below.

TABLE 2

| SEQ ID NO. | Amino acid sequences of peptides |
|---|---|
| 1 | RDCAE VFKSG HTTNG |
| 2 | VFKSG HTTNG IYTLT |
| 3 | HTTNG IYTLT FPNST |
| 4 | IYTLT FPNST EEIKA |
| 5 | FPNST EEIKA YCDME |
| 6 | EEIKA YCDME AGGGG |
| 7 | YCDME AGGGG WTIIQ |
| 8 | AGGGG WTIIQ RREDG |
| 9 | WTIIQ RREDG SVDFQ |
| 10 | RREDG SVDFQ RTWKE |
| 11 | SVDFQ RTWKE YKVGF |
| 12 | RTWKE YKVGF GNPSG |
| 13 | YKVGF GNPSG EYWLG |
| 14 | GNPSG EYWLG NEFVS |
| 15 | EYWLG NEFVS QLTNQ |
| 16 | NEFVS QLTNQ QRYVL |
| 17 | QLTNQ QRYVL KIHLK |
| 18 | QRYVL KIHLK DWEGN |
| 19 | KIHLK DWEGN EAYSL |
| 20 | DWEGN EAYSL YEHFY |
| 21 | EAYSL YEHFY LSSEE |
| 22 | YEHFY LSSEE LNYRI |
| 23 | LSSEE LNYRI HLKGL |
| 24 | LNYRI HLKGL TGTAG |
| 25 | HLKGL TGTAG KISSI |
| 26 | TGTAG KISSI SQPGN |
| 27 | KISSI SQPGN DFSTK |
| 28 | SQPGN DFSTK DGDND |
| 29 | DFSTK DGDND KCICK |
| 30 | DGDND KCICK CSQML |
| 31 | KCICK CSQML TGGWW |
| 32 | CSQML TGGWW FDACG |
| 33 | TGGWW FDACG PSNLN |
| 34 | FDACG PSNLN GMYYP |
| 35 | PSNLN GMYYP QRQNT |
| 36 | GMYYP QRQNT NKFNG |
| 37 | QRQNT NKFNG IKWYY |
| 38 | NKFNG IKWYY WKGSG |
| 39 | IKWYY WKGSG YSLKA |
| 40 | WKGSG YSLKA TTMMI |
| 41 | YSLKA TTMMI RPADF |

Figure 9:
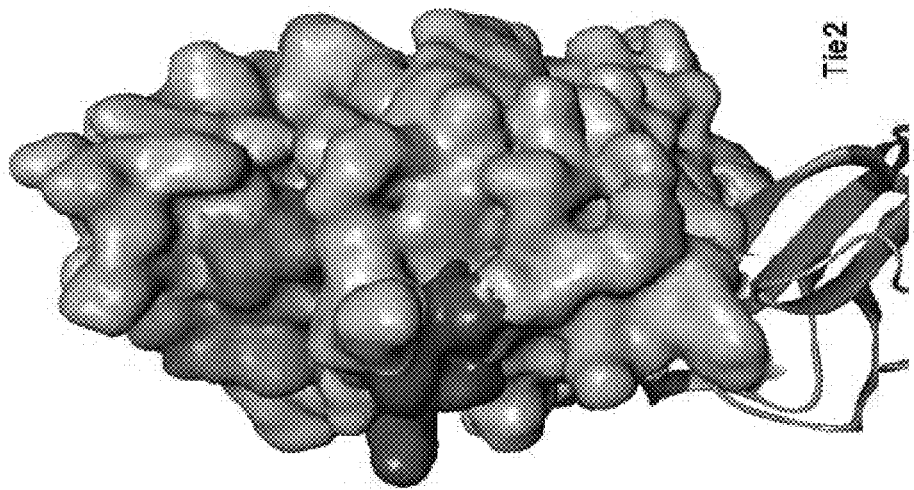
FIG. 9 is a table that illustrates amino acid sequences of Ang2 derived peptides and a 3-D structure image of receptor binding domain of Ang2, where the locations of the amino acid residues represented in yellow, green or red in the table are depicted in the same color in the picture. The sequence identification numbers of the peptides (SEQ ID NOs:1-41)are provided to the left of each peptide sequence.

Furthermore, the locations of the peptides on a 3D structure of Ang2 protein are shown in FIG. 9.

5.2. Inhibition of Binding Between Ang2 and Integrin by the Peptides

Figure 8:
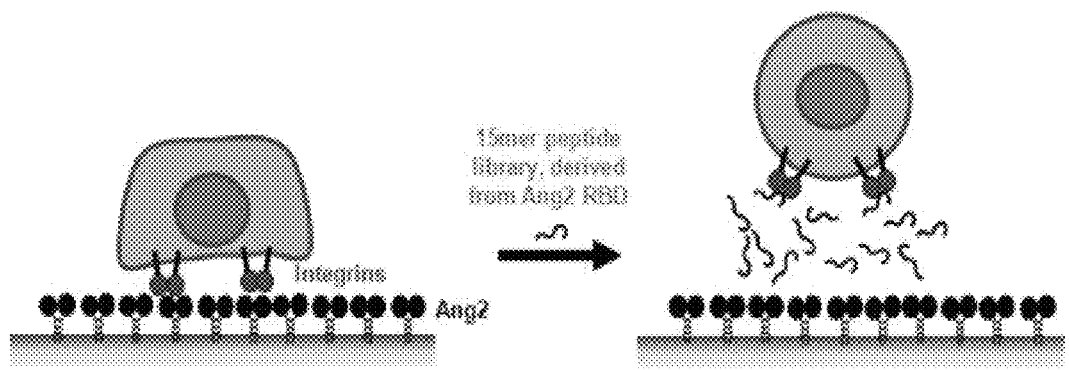
FIG. 8 is a schematic picture showing an experiment design for identifying Ang2-derived peptides which inhibit Ang2-depedent adhesion of U87MG cells

When Ang2-coated plates were treated with U87MG cells in accordance with the same methods as in Example 1.1, they were co-treated with one of the 41 peptides derived from Ang2 set forth in Table 2 to investigate the inhibition effects of the peptides against the adhesion of U87MG cells (see FIG. 8). Each peptide was treated at a concentration of 100 µg/ml and the number of U87MG cells treated with each peptide was about $4 \times 10^4$. The measurement of cell adhesion level was carried out in the same manner as Example 1.1. That is, after the addition of 200 µl of CellTiter-Glo reagent (Promega) diluted in IMDM at 1:1, their luminescence was measured at EnVision® Multilabel Reader (PerkinElmer) after 10 min.

The thus obtained results are shown in FIG. 10. As seen in FIG. 10, the treatment with the peptides having the amino acid sequences of SEQ ID Nos. 3, 4, 15 and 24 among the peptides of Table 2 reduced Ang2 dependent cell adhesion by 50% or more, when compared to the case with no treatment given (marked as +). The case that was solely blocked with BSA without Ang2 coating was used as a negative control (marked as −).

Example 6

Activity of Ang2 Derived Peptides

Figure 13:
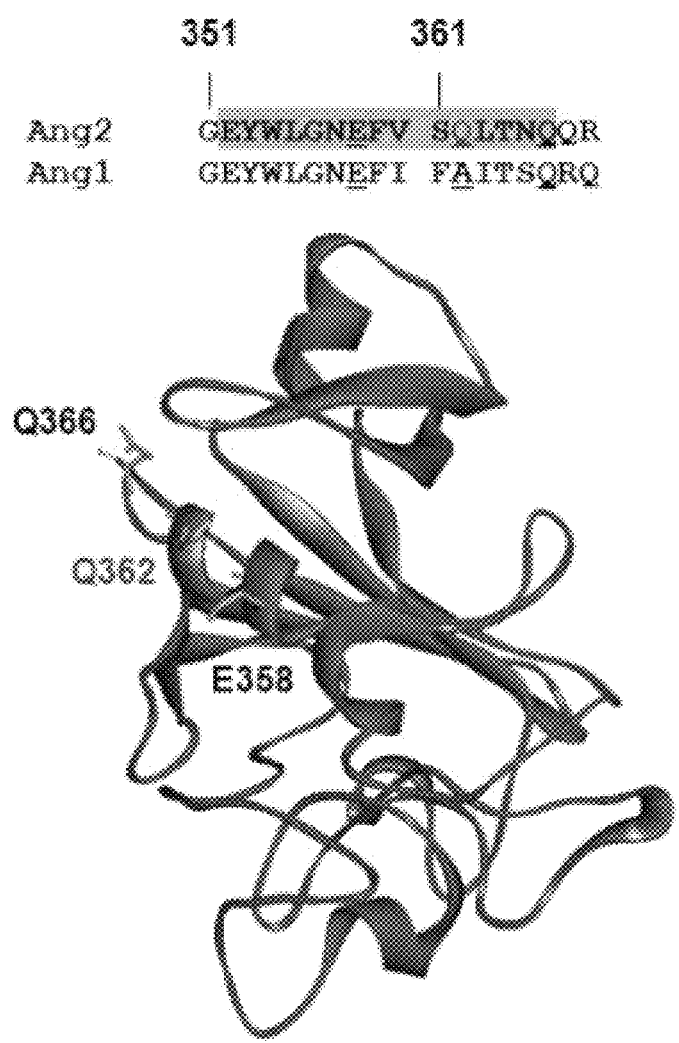
FIG. 13 is a picture showing the location of Ang2 derived peptide (SEQ ID No. 15) on a 3D structure of Ang2.

The location of the peptide having the amino acid sequence of SEQ ID No. 15, which had the best Ang2 dependent cell adhesion inhibition activity in Example 5.2 (hereafter, referred to as 'Peptide 15'), on the 3D structure of Ang2 protein is shown in FIG. 13 (shaded part of the amino acid sequences in FIG. 13 is Peptide 15). As seen in FIG. 13, Peptide 15 has amino acid sequences containing amino acids 352 to 366 of the Ang2 protein and, of them, the side chain of glutamine (Q) corresponding to $362^{nd}$ amino acid of the Ang2 protein is exposed to the outside in the 3D structure of the Ang2 protein.

In this Example, in order to reconfirm that this particular region of Ang2 binds integrin, the activity of a modified peptide where glutamine (Q), the $362^{nd}$ amino acid, which is an amino acid residue exposed to the outside on the 3D structure of the Ang2 protein, is substituted by alanine (A) (hereafter referred to as 'Q362A') and was compared to Ang2 protein that was not substituted.

First, glutamine corresponding to amino acid 362 of the Ang2 protein (SEQ ID No. 42) was substituted by alanine and probed with FLAG tag to prepare a FLAG-Ang2 protein modified form (Q362A). In accordance with the same methods as Example 3, after ELISA plates were coated with integrin (αVβ3), they were treated with 5 μg/ml of wild-type Ang2 protein (SEQ ID No. 42) and Q362A Ang2 protein, respectively, to compare levels of binding to integrin.

Figure 11:
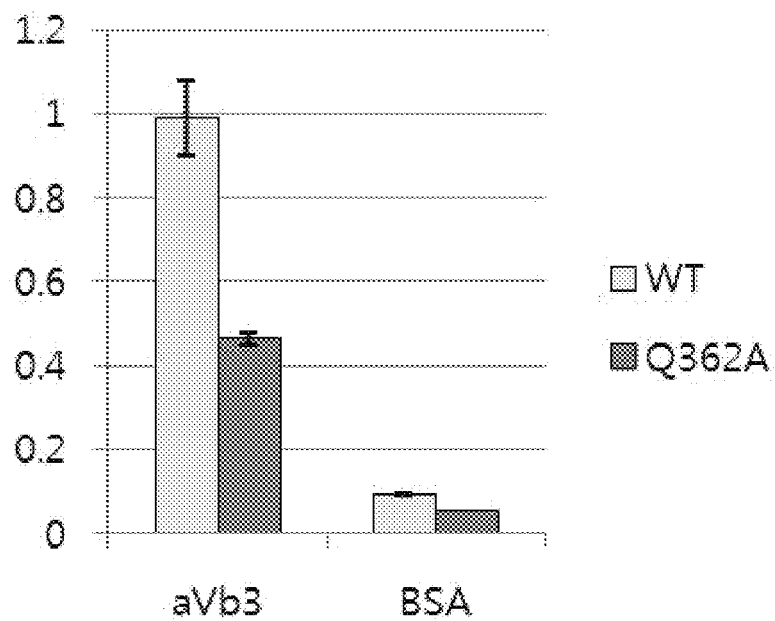
FIG. 11 is a graph showing the effects of Q362A mutation in Ang2 on the Ang2-integrin binding.

The thus obtained results are shown in FIG. 11. In the graph of FIG. 11, the y axis represents binding levels of each Ang2 protein to coated integrin αVβ3 or negative control BSA. As seen in FIG. 11, the binding level of Q362A to integrin was about 50% or less than the binding level of the wild type Ang2 peptide to integrin, indicating that Q362A modification of Ang2 peptide inhibits Ang2-integrin binding by 50% or more. Such results confirm that the modified region is the binding region between integrin and Ang2. In FIG. 11, BSA indicates a negative control which was blocked with BSA without integrin coating.

Figure 12:
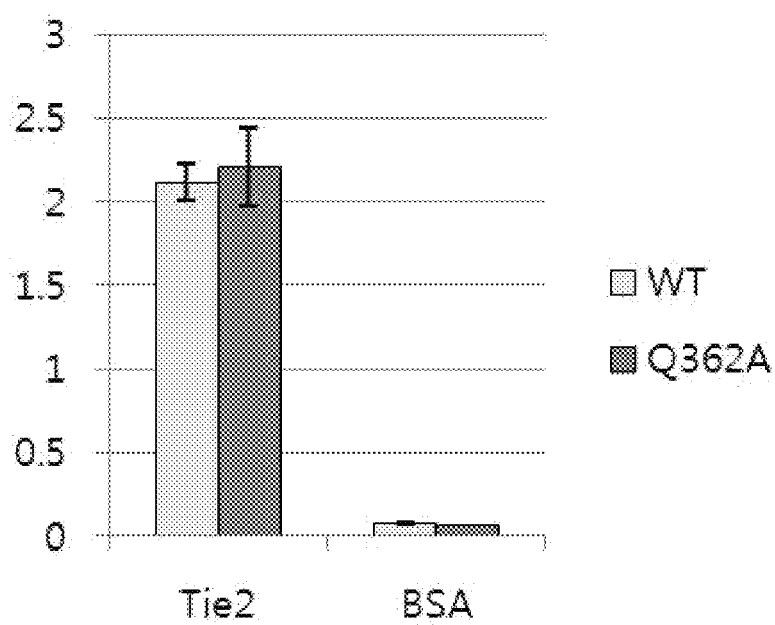
FIG. 12 is a graph showing the effects of Q362A mutation in Ang2 on the Ang2-Tie2 binding.

ELISA plates were coated with Tie2 proteins (Q02763, R&D systems), instead of integrin and then Ang2-Tie2 binding was observed in the same manner as above. The results are shown in FIG. 12. The Y axis represents binding levels of each Ang2 protein to coated Tie2 or negative control BSA. As seen in FIG. 12, the binding level of Q362A to Tie2 did not show any significant differences from the binding level of the wild type Ang2 peptide to Tie2, which indicates the modified region is not involved with Tie2-Ang2 binding.

The results of FIG. 11 and FIG. 12 confirm that the modified region of Ang2 peptide (the $362^{nd}$ amino acid region of Ang2) is a specific binding region to integrin.

Example 7

Cancer Cell Invasion

U87MG cells which underwent serum starvation for two days were detached using a cell dissociation solution (EDTA solution) and diluted in 0% serum IMDM media, and then $7.5 \times 10^4$ of the cells were each treated in an upper chamber of a matrigel-coated transwell chamber (24 wells, BD bio-science). Lower chambers were filled with a diluent obtained by diluting wild type Ang2 protein or its Q362A modified form (see Example 6) in 2% serum IMDM media at a concentration of 5 μg/ml. After 48 hours passed, the cells were dyed using calcein-AM solution (4 μg/ml; BD Biosciences) and observed using a fluorescence microscope to measure the number of the cells which invaded toward the bottom.

The results are shown in FIG. 14. The left part of FIG. 14 indicates the number of the cells that migrated to the lower chambers, and the right part illustrates the observation results of fluorescence treatment of the cells which migrated to the lower chambers, using a fluorescence microscope. In FIG. 14, '−' indicates a negative control where the lower chamber was not treated with Ang2 protein or its modified form. In FIG. 14, in comparison with wild type Ang2 protein, its Q362 modified form showed a remarkably low induction level of cancer cell invasion (approximately half or so). Such results indicate that the modified region of Ang2 protein which is specific to integrin (the $362^{nd}$ amino acid region of Ang2) is involved with cancer cell invasion (or migration) and further, can be construed to indicate that binding of Ang2 and integrin is involved with cancer cell migration and metastasis.

Example 8

Preparation of Peptibody (C-Body)

A peptibody (hereafter, named as 'C-body') was prepared by attaching peptides containing several copies of Ang2 Peptide 15 repeatedly at the N-terminal or the C-terminal of immunoglobulin Fc fragment (see FIG. 15).

When the C-body was used, it exhibited excellent cell adhesion inhibition effects even at a low concentration (e.g., 5 μg/ml).

The preparation of the C-body will be explained in more detail as follows. An Ang2 derived peptide-linker repeat fragment was prepared by selecting Peptide 15, which was determined to have excellent Ang2-dependent cell adhesion inhibition activity in Example 5.2, and designing a fragment where Peptide 15 and a linker repeat 4 times starting from N-terminal, i.e., N terminal-Peptide 15-Linker-Peptide 15-Linker-Peptide 15-Linker-Peptide 15-Linker-C terminal. Similarly, a linker-peptide repeat fragment having a structure of N terminal-Linker-Peptide 15-Linker-Peptide 15-Linker-Peptide 15-Linker-Peptide 15-C terminal was also prepared. In this example, the amino acid sequence of the linker used for the production of C-body is 'Gly-Gly-Gly-Ser.'

The C terminal of one of the above prepared Ang2 derived peptide-linker repeat fragments was fused with the N terminal of a Fc fragment of human immunoglobulin G1 (human IgG1), and the N terminal of the other linker portion was fused with the C terminal of the immunoglobulin Fc fragment, thereby producing a construct having a structure of (Ang2 derived peptide-linker repeat fragment)-(Fc fragment)-(Ang2 derived linker-peptide repeat fragment). The produced construct had the structure shown in FIG. 15 during its intracellular production by virtue of the dimer formation tendency of Fc.

Example 9

Ang2 Dependent Cell Adhesion Inhibition Activity by C-Body

When Ang2-coated plates were treated with U87MG cells in accordance with the same methods as in Example 1.1, they were co-treated with the C-body produced in Example 8 to investigate inhibition effects of C-body treatment on the adhesion of U87MG cells. The C-body was treated at a concentration of 20 μg/ml or 5 μg/ml, and the number of U87MG cells used was about $4 \times 10^4$ at each concentration.

Figure 16:
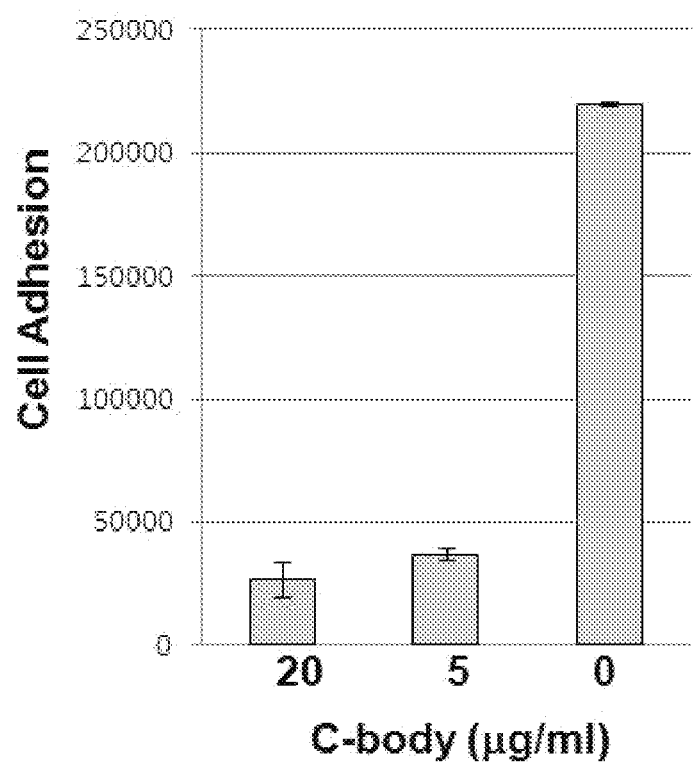
FIG. 16 is a graph showing the effect of C-body (FIG. 15) on U87MG cell adhesion.

Cell adhesion levels were measured in accordance with the same methods as Example 1.1 and shown in FIG. 16. As seen in FIG. 16, C-body treatment remarkably inhibited cell adhesion, in comparison with the case with no treatment (0 μg/ml).

Example 10

Ang2-Integrin Binding Inhibition by C-Body

The same methods as described in Example 4 were carried out, except that CHO cells co-transfected with cDNA of integrin (α5β1) and GFP were further treated with 10 μg/ml of C-body along with FLAG-Ang2, and the obtained flow cytometry analysis results are shown in FIG. 17.

In the top graph of FIG. 17, the y axis represents the expression of GFP which is a transfection marker, and the x axis represents binding level of integrin (α5β1) and Ang2. The bold dots represent an average of binding levels between integrin and Ang2 in several cells. As the slope of lines made of red dots in top parts of each graph decreases, the binding level with Ang2 increases. The red dots in the top graph of FIG. 17 were converted into linear-log scales, which are shown as the bottom graph. As seen in FIG. 17, C-body treatment remarkably inhibited binding between Ang2 and integrin. Vector is a negative control where no gene was expressed.

Figure 22:
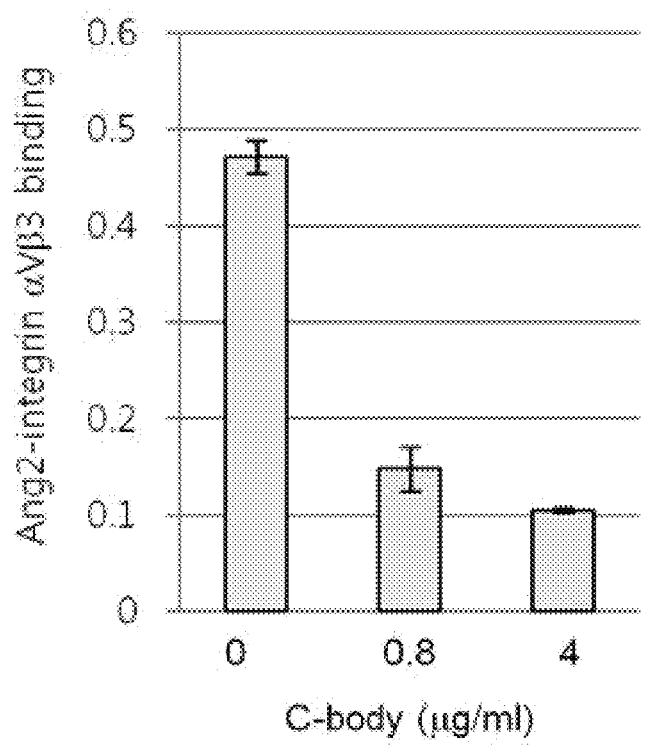
FIG. 22 is a graph showing the binding levels between integrin (αVβ3) and Ang2 when treated with C-body, according to the concentrations of C-body.

Furthermore, with the exception that that during the treatment of FLAG-Ang2, 0 μg/ml, 0.8 μg/ml, and 4 μg/ml of C-body were treated, the same methods as Example 3 were carried out to investigate binding level between integrin (αVβ3) and Ang2, and the results are shown in FIG. 22. As seen in FIG. 22, C-body inhibited binding between integrin (αVβ3) and Ang2 in a concentration-dependent manner.

Example 11

Signal Transduction Inhibition Activity by Ang2-Integrin Binding of C-Body

In accordance with Example 2 above, 6 wells were coated with 100 μg/ml of poly-L-lysine, 10 μg/ml of Ang2, or 10 μg/ml of fibronectin, respectively, and 2 ml of a U87MG cell suspension (about $3 \times 10^5$ cells/ml) was added to the surfaces blocked with 2% (v/v) BSA to perform a cell adhesion test. When the cells were added, 5 μg/ml of C-body was or was not treated with regard to each coating condition. After the induction of cell adhesion in a $CO_2$ incubator of 37° C. for 2 hours, the adhered cells and non-adhered cells were collected and they subjected to western blotting using an antibody which recognizes only FAK phosphorylated at tyrosine of No. 397 (Life Technologies) or an antibody which recognizes only FAK phosphorylated at serine of No. 910 (Life Technologies) to investigate the phosphorylation level of FAK.

Figure 18:
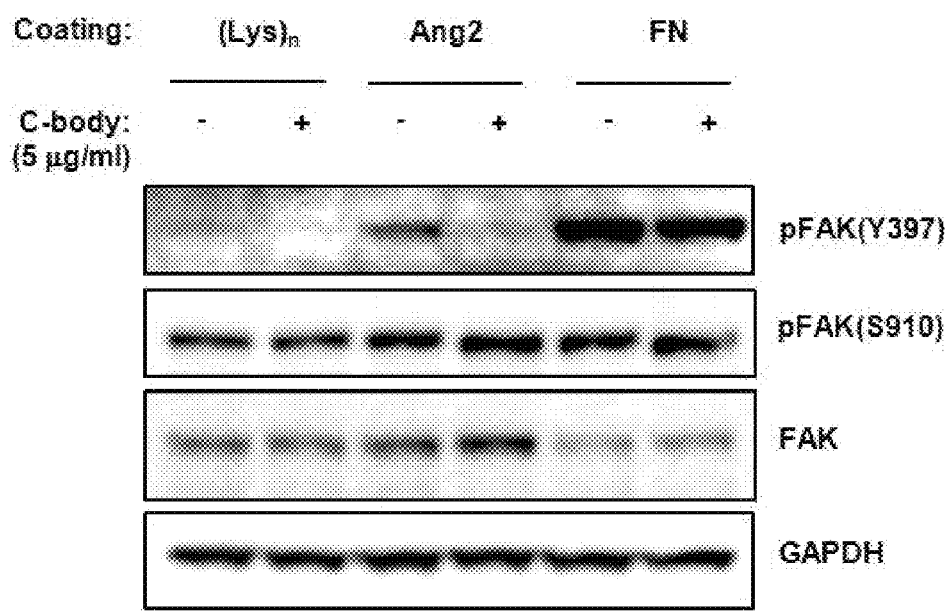
FIG. 18 is a gel image that shows FAK phosphorylation levels after U87MG cell line was adhered to poly-L-lysine, Ang2 or fibronectin-coated wells with or without C-body treatment, measured by their western blotting using anti-phospho FAK antibody.

The obtained results are shown in FIG. 18. As seen in FIG. 18, each of the three coating conditions made little difference in expression levels of overall FAK (focal adhesion kinase) (third panel) or phosphorylation of serine of No. 910 of FAK regardless of the presence of C-body, but the phosphorylation of tyrosine of No. 397 was highly reduced by C-body only under Ang2 coating condition since autophosphorylation occurred due to integrin's clustering. This means that C-body does not inhibit the binding of fibronectin and integrin and it selectively inhibits Ang2-integrin binding only and at the same time, which suggests that the Ang2-integrin binding can cause integrin-dependent signal transduction such as phosphorylation of FAK. GAPDH was used as a control for the quantity of the total proteins to be loaded on gels.

Example 12

Presence or Absence of Ang2-Tie2 Binding Inhibition by C-Body

As in Example 6, while Tie2-coated ELISA plates were being incubated after the addition of 100 μl of FLAG-Ang2 (5 μg/ml), they were treated or not treated with C-body at a concentration of 5 μg/ml to examine any changes in Ang2-Tie2 binding according to the presence or absence of C-body.

Figure 19:
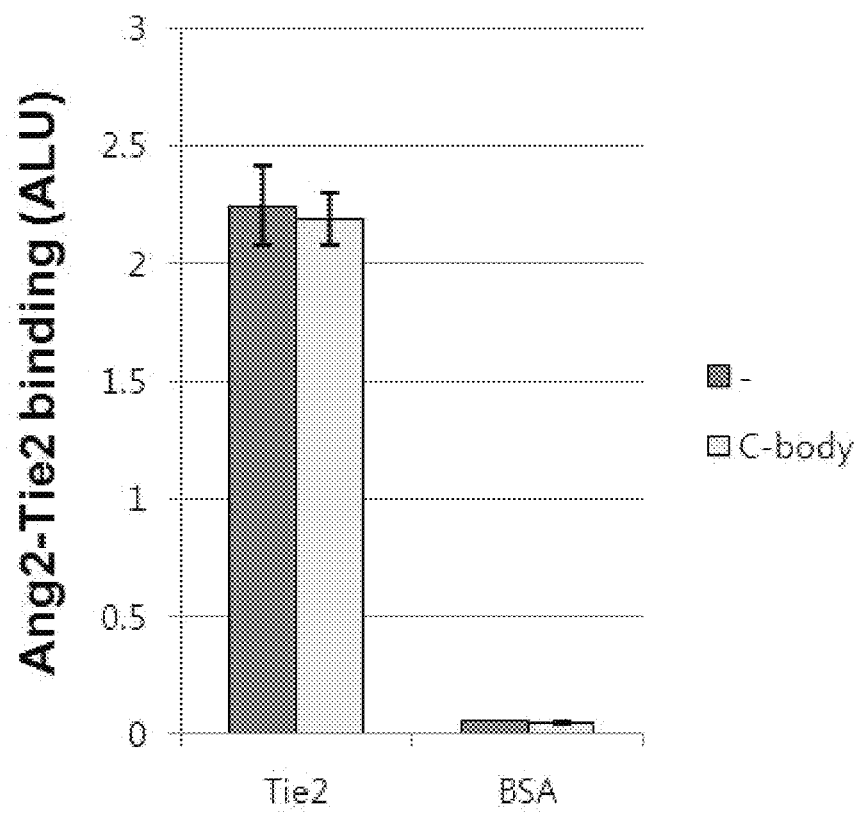
FIG. 19 is a graph showing the effect of C-body in Ang2-Tie2 binding, measured by ELISA.

The thus obtained results are shown in FIG. 19. As seen in FIG. 19, when the binding strength of Ang2 and Tie2 was measured, both of the cases where C-body was not contained (dark gray; marked as −) and the case where it was contained (light gray; marked as C-body) did not show any significant differences in Ang2-Tie2 binding. Hence, the C-body did not exhibit inhibition effects on Tie2-Ang2 binding. That is, it can be confirmed that C-body selectively inhibits integrin-Ang2 binding only.

Example 13

Migration Inhibitory Activity of Lymphatic Endothelial Cells (LEC) by C-Body

To each well of the lower chambers of CIM-plate 16 (GE healthcare) was added EBM media (Lonza) to which 2% (v/v) fetal bovine serum (FBS) was added, and 2 μg/ml of Ang2 along with either 10 μg/ml of C-body produced in Example 8, or μg/ml of Fc, a negative control, (human IgG1). The plates were assembled with the upper chambers coated with fibronectin. 40,000 lymphatic endothelial cells (LEC; Lonza) resuspended in serum-free media were added to each well, which was then equipped to xCelligence Realtime cell analyzer (GE Healthcare), and the impedance between the upper chambers and lower chambers was measured and marked for 30 hours to quantify cell migration.

Figure 20:
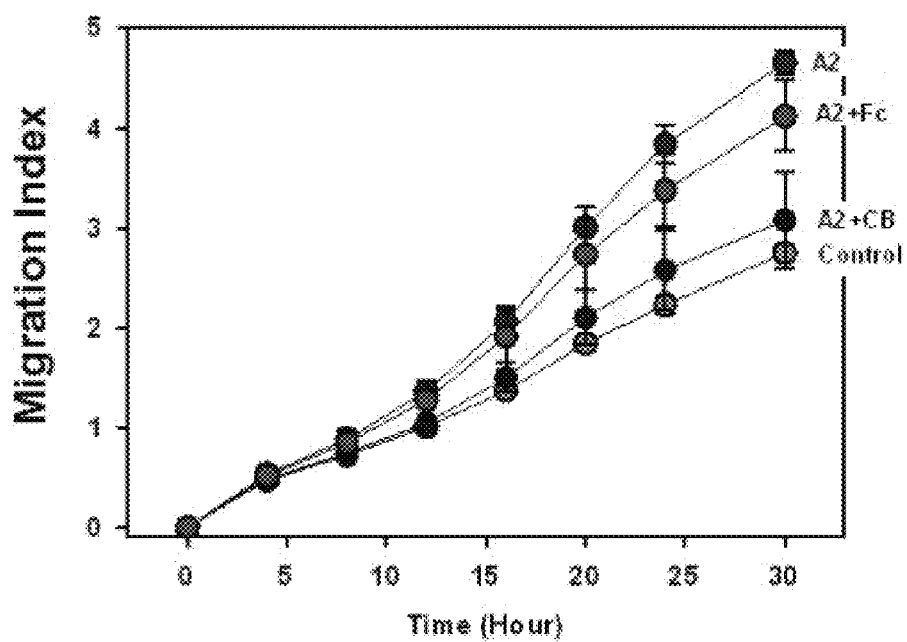
FIG. 20 is a graph showing the migration levels of lymphatic endothelial cells when treated with C-body or Fc (control group) along with Ang2.
Figure 21:
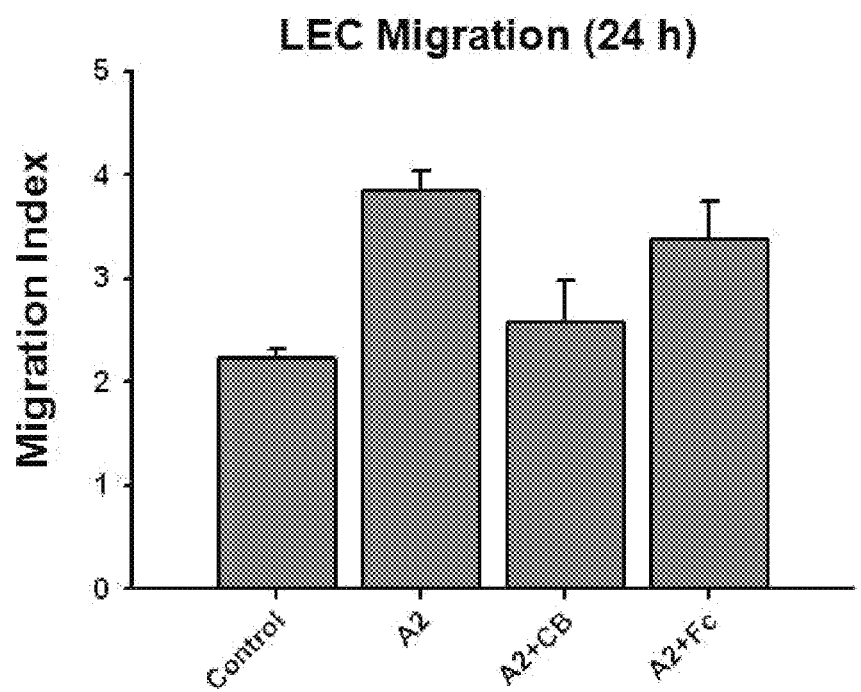
FIG. 21 is a graph showing the migration levels of lymphatic endothelial cells to lower chambers when treated with C-body or Fc (control group) along with Ang2, the results measured after 24 hours of cell migration induction.

The obtained results are shown in FIG. 20 and FIG. 21. FIG. 20 shows cell migration levels according to time, and FIG. 21 shows cell migration levels after 24 hours of cell migration induction as a bar graph. The control set forth in FIG. 20 and FIG. 21 refers to a negative control with no treatment given.

As seen in FIG. 20 and FIG. 21, cancer cell migration was remarkably reduced to the control level by virtue of C-body treatment.

What is claimed is:

1. A polypeptide molecule comprising one or two first peptides and a second peptide, wherein:
   each first peptide inhibits the binding of Ang2 and integrin and is, independently,
   (1) a peptide consisting of 5 to 25 consecutive amino acids of SEQ ID NO: 43 including the amino acids from the 11th to 15th positions of SEQ ID NO: 43, or
   (2) a peptide repeat wherein the peptide of (1) is repeated 2 to 20 times;
   the second peptide is a heavy chain or light chain of an antibody, a constant region of a heavy chain or light chain of an antibody, or an Fc fragment of an antibody; and
   at least one of the one or two first peptides is coupled with the second peptide at the N terminus or the C terminus of the second peptide, or one first peptide is coupled to the N terminus of the second peptide and another first peptide is coupled to the C terminus of the second peptide.

2. The polypeptide molecule of claim 1, further comprising a linker coupling at least one of the one or two first peptides with the second peptide, or a linker between repeating sequences of the one or two first peptides, or both.

3. A polypeptide complex comprising 2 to 4 polypeptide molecules of claim 1.

4. A polypeptide complex comprising 2 to 4 polypeptide molecules of claim 2.

5. The polypeptide molecule of claim 1, wherein each of the one or two first peptides, independently, consists of SEQ ID NO: 15, 16, or 17.

6. The polypeptide molecule of claim 2, wherein the linker comprises the amino acid sequence GGGS (SEQ ID NO: 45).

7. The polypeptide molecule of claim 1, wherein the second peptide is a Fc fragment of an antibody.

8. The polypeptide molecule of claim 1, wherein the second peptide is a Fc fragment of an antibody.

9. The polypeptide molecule of claim 5, wherein the second peptide is a Fc fragment of an antibody.

* * * * *